(12) United States Patent
Kawaura et al.

(10) Patent No.: US 9,999,491 B2
(45) Date of Patent: Jun. 19, 2018

(54) PUNCTURE DEVICE AND PUNCTURE APPARATUS

(71) Applicant: TERUMO KABUSHIKI KAISHA, Shibuya-ku (JP)

(72) Inventors: Masakatsu Kawaura, Sunnyvale, CA (US); Shigeki Ariura, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 122 days.

(21) Appl. No.: 14/497,708

(22) Filed: Sep. 26, 2014

(65) Prior Publication Data

US 2015/0073206 A1 Mar. 12, 2015

Related U.S. Application Data

(63) Continuation of application No. PCT/JP2013/056681, filed on Mar. 11, 2013.

(30) Foreign Application Priority Data

Mar. 30, 2012 (JP) .................................. 2012-079036

(51) Int. Cl.
*A61F 2/00* (2006.01)
*A61B 17/04* (2006.01)
(Continued)

(52) U.S. Cl.
CPC ........ *A61F 2/0045* (2013.01); *A61B 17/0469* (2013.01); *A61B 17/0482* (2013.01);
(Continued)

(58) Field of Classification Search
CPC .... A61F 2/0004; A61F 2/0009; A61F 2/0031; A61F 2/0036; A61F 2/0045;
(Continued)

(56) References Cited

U.S. PATENT DOCUMENTS 6,245,082 B1 6/2001 Gellman et al.
6,494,887 B1 12/2002 Kaladelfos
(Continued)

FOREIGN PATENT DOCUMENTS

CA 2 777 160 A1 6/2011
CN 1382029 A 11/2002
(Continued)

OTHER PUBLICATIONS

International Search Report (PCT/ISA/210) dated May 14, 2013, by the Japanese Patent Office as the International Searching Authority for International Application No. PCT/JP2013/056681.
(Continued)

*Primary Examiner* — Catherine B Kuhlman
*Assistant Examiner* — Carrie R Dorna
(74) *Attorney, Agent, or Firm* — Buchanan Ingersoll & Rooney PC

(57) ABSTRACT

A puncture device, a puncture apparatus, and a method are disclosed, the puncture apparatus including a puncture device for puncturing a biological tissue, a urethral-insertion member, a vaginal insertion member, and a supporting member which supports the urethral-insertion member, vaginal insertion member and a puncture member of the puncture device. The puncture device includes a puncture needle for puncturing a biological tissue, a shaft portion and a connection portion for connecting the puncture needle and the shaft portion to each other, and an implant assembly positioned at a distal end of the puncture needle and having a needle tip portion for puncturing a biological tissue and a biological tissue supporting implant. The puncture needle has a form of a pipe and has a tubular portion. The biological tissue supporting implant is accommodated in the hollow portion.

10 Claims, 23 Drawing Sheets

(51) Int. Cl.
  *A61B 17/34* (2006.01)
  *A61B 17/00* (2006.01)
  *A61B 17/06* (2006.01)

(52) U.S. Cl.
  CPC ...... *A61B 17/0491* (2013.01); *A61B 17/3403* (2013.01); *A61B 17/3468* (2013.01); *A61F 2/0063* (2013.01); *A61B 2017/00805* (2013.01); *A61B 2017/061* (2013.01); *A61B 2017/0608* (2013.01); *A61B 2017/3407* (2013.01); *A61B 2017/3409* (2013.01); *A61F 2002/0072* (2013.01)

(58) Field of Classification Search
  CPC ........... A61F 2/0063; A61F 2002/0072; A61B 17/0469; A61B 17/0482; A61B 17/0625; A61B 17/3468; A61B 2017/00805
  See application file for complete search history.

(56) References Cited

U.S. PATENT DOCUMENTS

| | | | |
|---|---|---|---|
| 6,911,003 | B2 | 6/2005 | Anderson et al. |
| 2002/0055748 | A1 | 5/2002 | Gellman et al. |
| 2004/0122474 | A1 | 6/2004 | Gellman et al. |
| 2005/0004576 | A1* | 1/2005 | Benderev ........... A61B 17/0401 606/300 |
| 2006/0089525 | A1* | 4/2006 | Mamo ................ A61B 17/0401 600/37 |
| 2007/0038017 | A1 | 2/2007 | Chu |
| 2007/0156012 | A1* | 7/2007 | Tracey ............... A61B 17/0625 600/30 |
| 2008/0132753 | A1 | 6/2008 | Goddard |
| 2010/0280309 | A1* | 11/2010 | Von Pechmann ......................... A61B 17/00234 600/37 |

FOREIGN PATENT DOCUMENTS

| | | |
|---|---|---|
| JP | 2001-511686 A | 8/2001 |
| JP | 2003-512123 A | 4/2003 |
| JP | 2007-260422 A | 10/2007 |
| JP | 2010-99499 A | 5/2010 |
| WO | WO 98/35606 A2 | 8/1998 |
| WO | WO 98/35616 A1 | 8/1998 |
| WO | WO 01/30246 A1 | 5/2001 |
| WO | WO 2003/075792 A1 | 9/2003 |

OTHER PUBLICATIONS

Partial Supplementary European Search Report dated Oct. 1, 2015 issued by the European Patent Office in corresponding European Patent Application No. 13768935.2 (5 pages).

Office Action dated Feb. 3, 2016 by the Chinese Patent Office in corresponding Chinese Patent Application No. 201380017963.6.

* cited by examiner

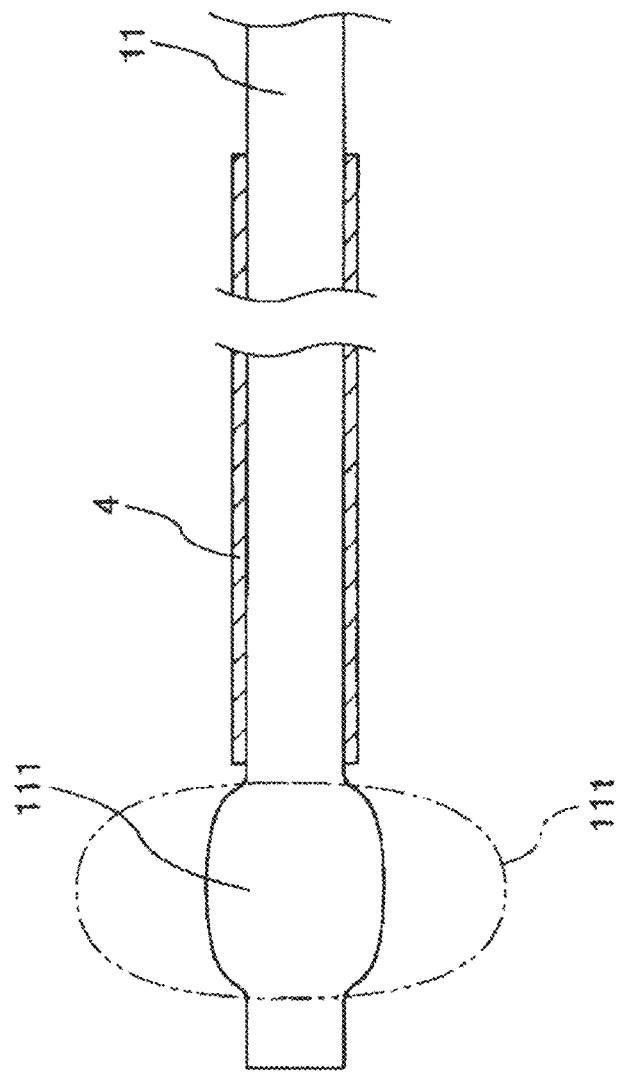

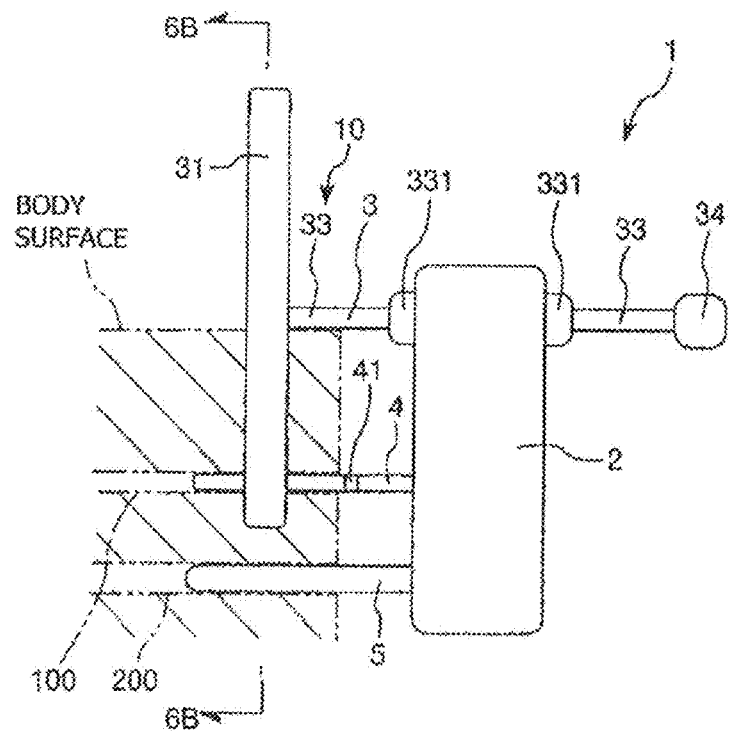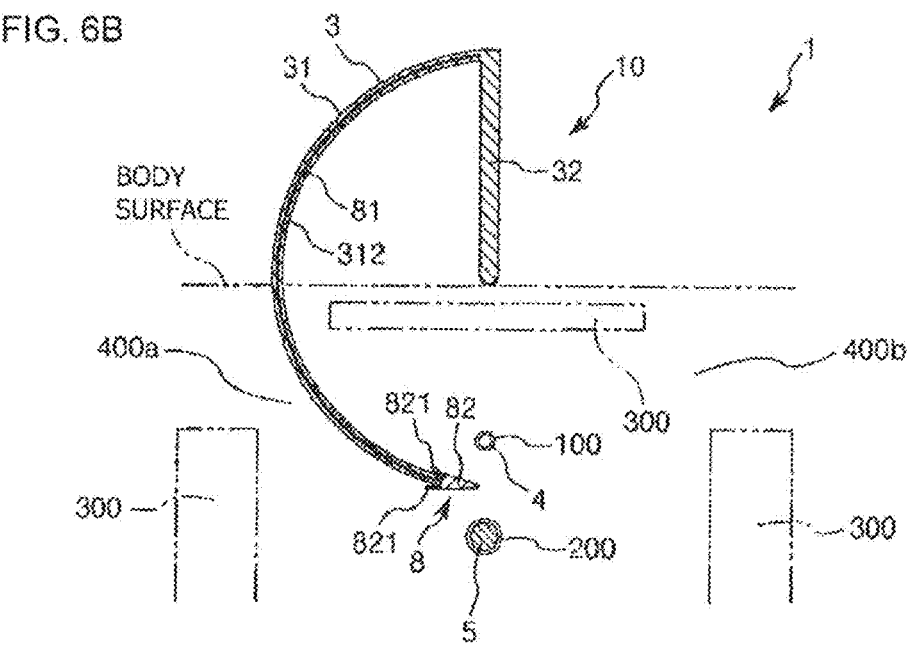

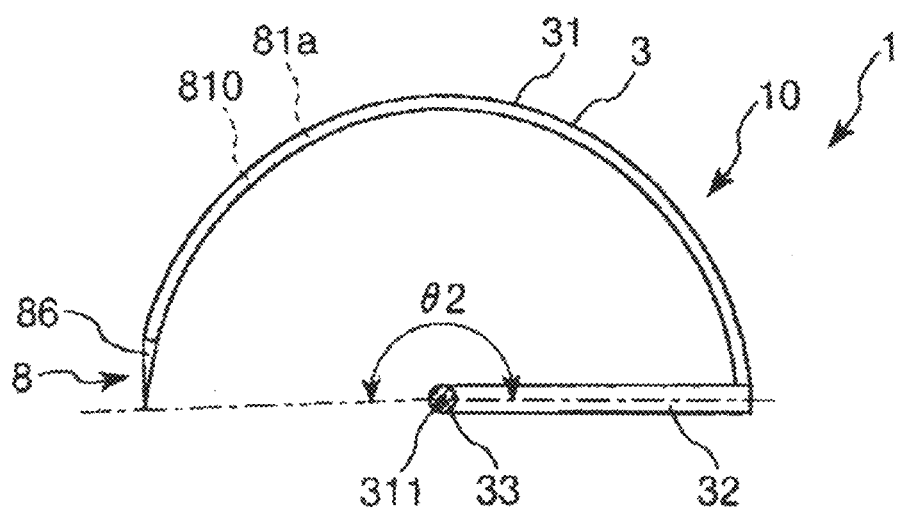
FIG.11

PUNCTURE DEVICE AND PUNCTURE
APPARATUS

CROSS-REFERENCES TO RELATED
APPLICATIONS

This application is a continuation of International Application No. PCT/JP2013/056681 filed on Mar. 11, 2013, and claims priority to Japanese Application No. 2012-079036 filed on Mar. 30, 2012, the entire content of both of which is incorporated herein by reference.

TECHNICAL FIELD

The present disclosure relates to a puncture device and a puncture apparatus.

BACKGROUND DISCUSSION

If a person suffers from a urinary incontinence, for example, if a person suffers from a stress urinary incontinence, then urine leakage can be caused by application of abdominal pressure during a normal exercise or by laughing, coughing, sneezing and the like. The cause of this may be, for example, that the pelvic floor muscle which is a muscle for supporting the urethra is loosened by birth or the like.

For the treatment of urinary incontinence, a surgical treatment is effective, in which there is used, for example, a belt-shaped biological tissue supporting implant (or biological tissue supporting indwelling article) called a "sling." The sling is indwelled inside the body and the urethra is supported by the sling (for example, U.S. Pat. No. 6,911,003). In order to indwell the sling inside the body, an operator would incise the vagina with a surgical knife, dissect a region between the urethra and the vagina, and communicate the dissected region and the outside with each other through an obturator foramen using a puncture needle or the like. Then, in such a state, the sling is indwelled into the body.

However, if the vagina is incised once, a situation may occur that the sling is exposed to the inside of the vagina from a wound caused by the incision of the vagina, and complications may be caused by an infection from the wound or the like. Further, since the vagina is incised, there is such a defect that the invasion is relatively great and the burden on the patient is relatively heavy. Further, the urethra or the like may be damaged in the course of the procedure by the operator. In addition, the fingertip of the operator may be damaged or injured.

SUMMARY

In accordance with an exemplary embodiment, a puncture device and a puncture apparatus are disclosed, by which a biological tissue supporting implant can be buried into a living body, in which the burden on the patient is relatively light, the safety of the patient is relatively high and also the safety of the operator is relatively high.

In accordance with an exemplary embodiment, a puncture device is disclosed, which can include a puncture needle having a hollow portion, a needle tip portion positioned at a distal end of the puncture needle and configured to puncture a biological tissue and an elongated biological tissue supporting implant accommodated in the hollow portion of the puncture needle and configured to be buried into a living body to support the biological tissue.

In the puncture device of the present disclosure, for example, the needle tip portion can be removably held by or fixed to a distal end portion of the biological tissue supporting implant.

In the puncture device of the present disclosure, for example, the biological tissue supporting implant can include a belt-like element configured to attach to a biological tissue, a first string-like element connected at a proximal end of the first string-like element to a distal end of the belt-like element, a second string-like element connected at a distal end of the second string-like element to a proximal end of the belt-like element and a holding member connected to a proximal end of the second string-like element and removably held by a proximal end of the puncture needle, the needle tip portion being removably held by or fixed to a distal end of the first string-like element.

In the puncture device of the present disclosure, for example, the needle tip portion can have an anchoring effect of helping prevent the needle tip portion from returning to an opposite direction to a puncturing direction of the needle tip portion.

In the puncture device of the present disclosure, for example, the needle tip portion can be fixedly mounted at or integrated with a distal end portion of the puncture needle.

In the puncture device of the present disclosure, for example, the puncture needle can have a variable length.

In the puncture device of the present disclosure, for example, the puncture needle can have a flattened shape as viewed in a longitudinal direction of the puncture needle, and the biological tissue supporting implant can have a belt-like portion, which is attached to a biological tissue.

In accordance with an exemplary embodiment, the puncture device of the present disclosure is configured such that the puncture needle has a curved portion along a longitudinal direction of the puncture needle.

In accordance with an exemplary embodiment, the puncture device of the present disclosure is configured such that the puncture device can be installed for rotational movement.

In accordance with an exemplary embodiment, a puncture apparatus is disclosed, which includes the puncture device of the present disclosure, a urethral-insertion member of a longitudinal shape configured to be inserted into a urethra and restriction means for restricting, when the puncture device is rotationally moved to puncture a biological tissue, a positional relationship between the puncture device and the urethral-insertion member such that the needle tip portion passes at a farther-position side from the center of rotational movement of the puncture device than the urethral-insertion member.

In accordance with an exemplary embodiment, the puncture apparatus of the present disclosure further includes a vaginal insertion member of a longitudinal shape configured to be inserted into a vagina, wherein the restriction means can restrict a positional relationship between the puncture device and the vaginal insertion member such that, when the puncture device is rotationally moved to puncture a biological tissue, the needle tip portion does not collide with the vaginal insertion member.

In accordance with an exemplary embodiment, the puncture apparatus of the present disclosure is configured such that the puncture device has a shaft portion which provides a rotational axis of the rotational moment, and the restriction means includes a supporting member which supports the shaft portion for rotational movement and supports the urethral-insertion member and the vaginal insertion member.

In the puncture apparatus of the present disclosure, for example, at least one of the urethral-insertion member and the vaginal insertion member has a suction means capable of attracting a biological tissue to the urethral-insertion member and/or the vaginal insertion member.

In the puncture apparatus of the present disclosure, for example, the positional relationship between the urethral-insertion member and the vaginal insertion member can be variable.

In accordance with an exemplary embodiment of the present disclosure, a biological tissue supporting implant can be buried into a living body readily, and when the biological tissue supporting implant is buried, the burden on the patient is relatively light and the safety of the patient is relatively high. The safety of the operator is also relatively high.

For example, where the puncture apparatus includes the restriction means for restricting the positional relation between the puncture device and the urethral-insertion member such that, when the puncture device rotationally moves to puncture the biological tissue, the needle tip portion passes the farther-position side from the center of rotational movement of the puncture device than the urethral-insertion member, when the puncture apparatus is to be used for the treatment of woman's urinary incontinence, the urethral-insertion member of the puncture apparatus is inserted into a urethra, and the puncture device is rotationally moved so that the living body is punctured by the puncture device. Since the needle tip portion passes the farther-position side from the center of rotational movement of the puncture device than the urethral-insertion member, the puncture needle can puncture the living body avoiding the urethra. Consequently, the puncture device can be prevented from puncturing the urethra. Further, the fingertip of the operator can be prevented from being punctured by the puncture device.

Further, when the biological tissue supporting implant for the treatment of urinary incontinence is to be buried, no incision of the vaginal wall is necessary, and the biological tissue supporting implant can be buried by a relatively low invasive manual procedure. Further, as in a case in which the vagina is incised, the biological tissue supporting implant can be exposed to the inside of the vagina through a wound caused by the incision or that such complications as an infection from the wound occur can be prevented. Therefore, the biological tissue supporting implant can be buried in relatively high safety and with relative certainty.

Further, since the biological tissue supporting implant is accommodated in the hollow portion of the puncture needle, the biological tissue supporting implant can be buried into a living body readily.

In accordance with an exemplary embodiment, a puncture apparatus is disclosed, comprising: a puncture device configured to have a rotational motion, the puncture device comprising: a puncture needle having a hollow portion, the puncture needle having a portion curved along a longitudinal direction of the puncture needle; a needle tip portion positioned at a distal end of the puncture needle and configured to puncture a biological tissue; and an elongated biological tissue supporting implant accommodated in the hollow portion of the puncture needle and configured to be buried into a living body to support the biological tissue; a urethral-insertion member of a longitudinal shape configured to be inserted into a urethra; and restriction means for restricting, when the puncture device is rotationally moved to puncture the biological tissue, a positional relationship between the puncture device and the urethral-insertion member such that the needle tip portion passes at a farther-position side from the center of rotational movement of the puncture device than the urethral-insertion member.

In accordance with an exemplary embodiment, a method is disclosed of forming a path in a living body comprising: placing a puncture needle of a puncture device into a portion of a living body, the puncture needle having a hollow portion, a curved portion along a longitudinal direction of the puncture needle, and a needle tip portion positioned at a distal end of the puncture needle and configured to puncture a biological tissue; accommodating an elongated biological tissue supporting implant in the hollow portion of the puncture needle and configured to be buried into the living body to support the biological tissue; inserting an urethral-insertion member of a longitudinal shape into a urethra; and restricting, when the puncture device is rotationally moved to puncture the biological tissue, a positional relationship between the puncture device and the urethral-insertion member such that the needle tip portion passes at a farther-position side from the center of rotational movement of the puncture device than the urethral-insertion member.

BRIEF DESCRIPTION OF THE DRAWINGS

FIG. 4 is a cross sectional view illustrating a state in which a balloon catheter is inserted in a urethral-insertion member of the puncture apparatus depicted in FIG. 1.

FIGS. 6(a) and 6(b) are views illustrating an operation procedure of the puncture apparatus depicted in FIG. 1 with FIG. 6(b) taken along the section line 6B-6B in FIG. 6(a).

FIG. 11 is a cross sectional view taken along the section line 11-11 in FIG. 10.

DETAILED DESCRIPTION

Figure 1:
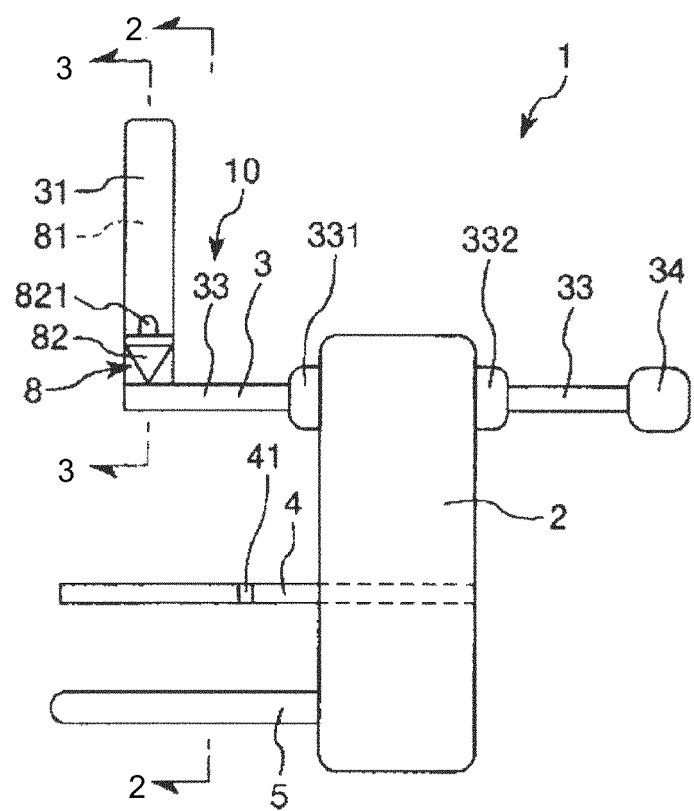
FIG. 1 is a lateral view depicting a first embodiment of a puncture apparatus of the present disclosure.

FIGS. 1-26 illustrate features and operational aspects of exemplary embodiments of the puncture apparatus as disclosed. FIGS. 1-9 depict a first exemplary embodiment of the puncture apparatus of the present disclosure. In FIG. 5(b), FIG. 6(b), FIG. 7(b), FIG. 8(b) and FIG. 9, slanting lines for a living body are omitted so as to be easily viewable. In the description, which follows, the left side in FIG. 1, FIG. 4, FIG. 5(a), FIG. 6(a), FIG. 7(a) and FIG. 8(a) is the "distal end" and the right side is the "proximal end."

The puncture apparatus 1 shown in the drawings is an apparatus to be used for the treatment of woman's urinary incontinence, for example, to be used when a biological tissue supporting implant for the treatment of urinary incontinence is buried into the inside of the living body. The biological tissue supporting implant can be a buriable tool for the treatment of woman's urinary incontinence, for example, an elongated tool to be buried into the living body for supporting the urethra (biological tissue), for example, a tool for supporting, for example, when it is intended to move the urethra to the vaginal wall side, the urethra tension-free or so as to pull the urethra in a direction in which the urethra is spaced away from the vaginal wall. For the biological tissue supporting implant, for example, an elongated object having flexibility can be used.

Figure 2:
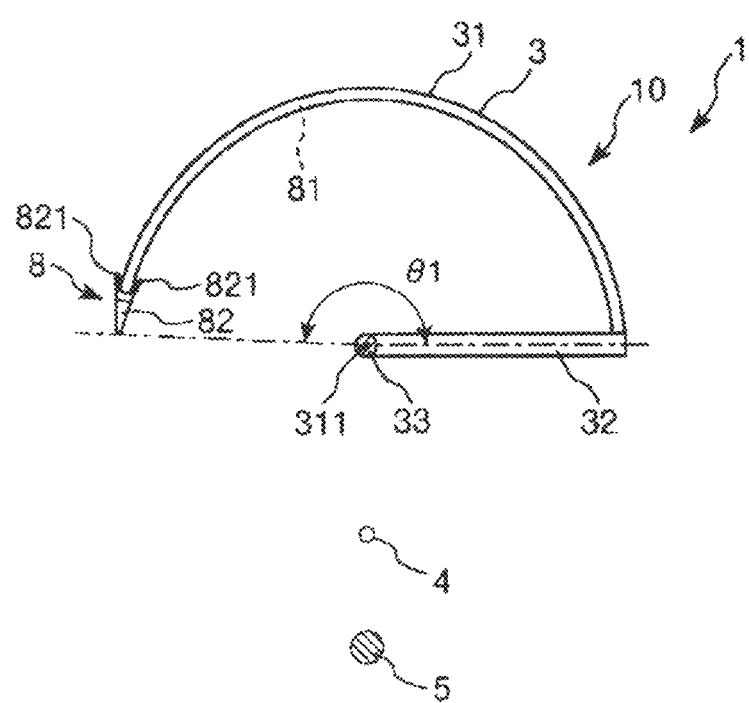
FIG. 2 is a cross sectional view taken along the section line 2-2 in FIG. 1.
Figures 3A, 3B:
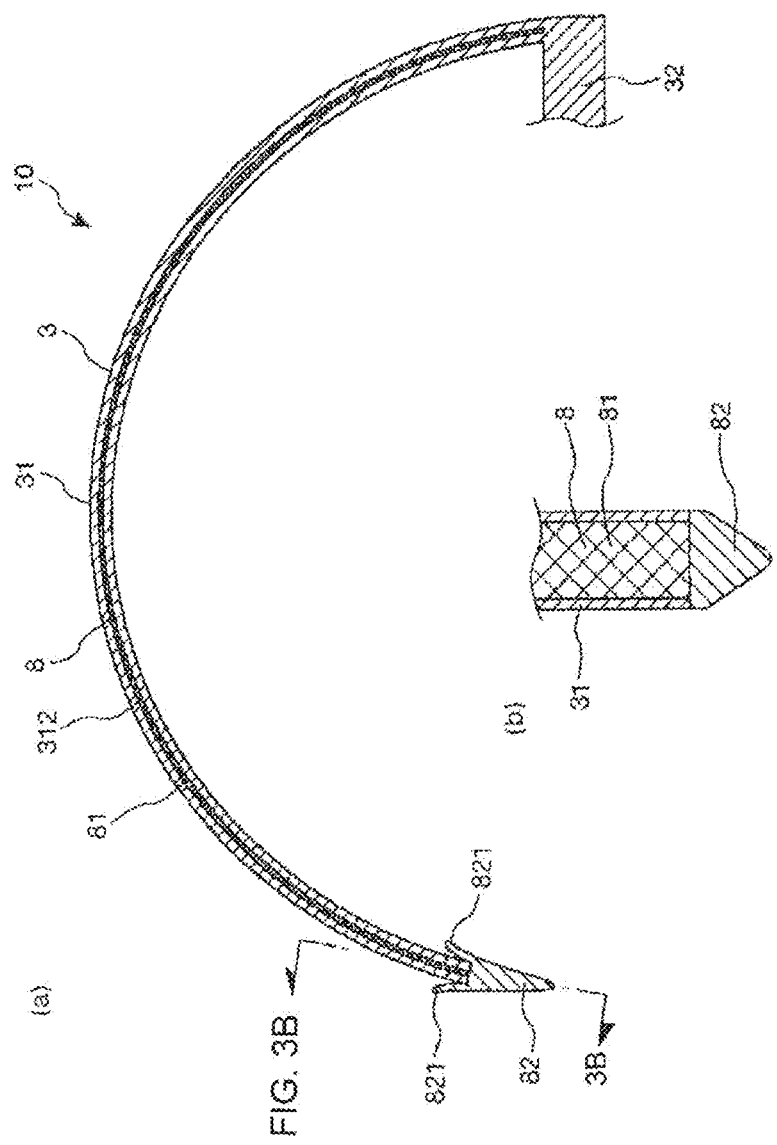
FIG. 3(a) is a cross sectional views of a puncture device of the puncture apparatus depicted along the section line 3-3 in FIG. 1.
FIG. 3(b) is a cross sectional view of the puncture device of the puncture apparatus depicted along the section line 3B-3B in FIG. 3(a).
Figure 5A:
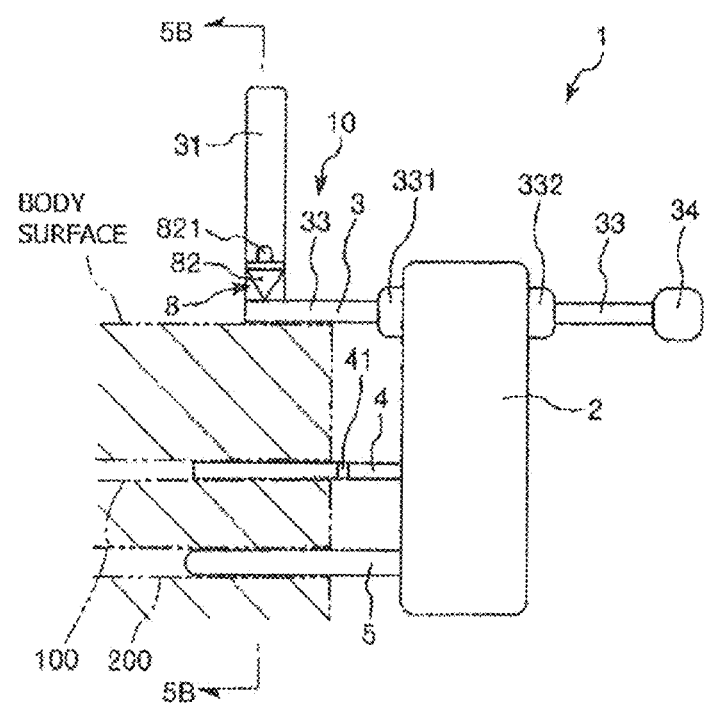
FIGS. 5(a) and 5(b) are views illustrating an operation procedure of the puncture apparatus depicted in FIG. 1 with FIG. 5(b) taken along the section line 5B-5B in FIG. 5(a).
Figure 5B:
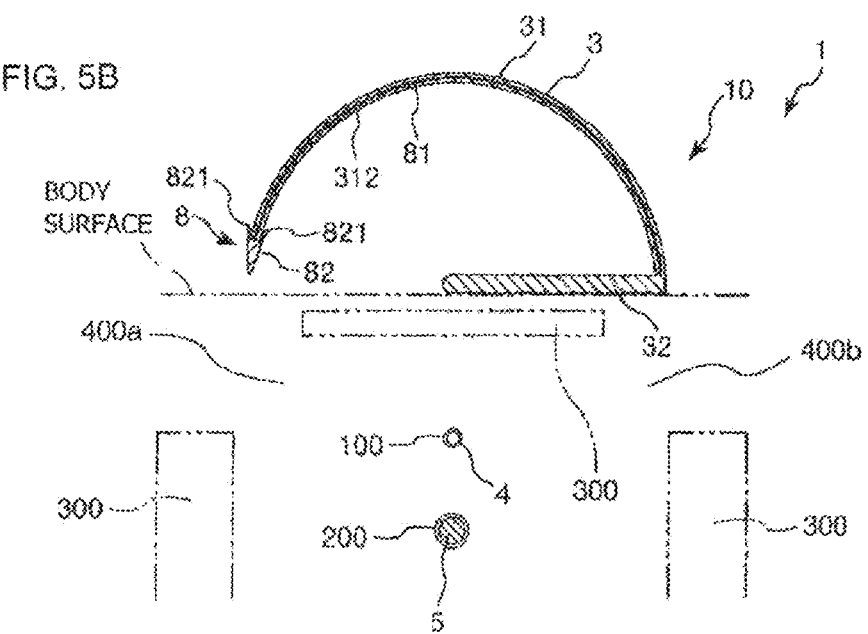
Figure 7A:
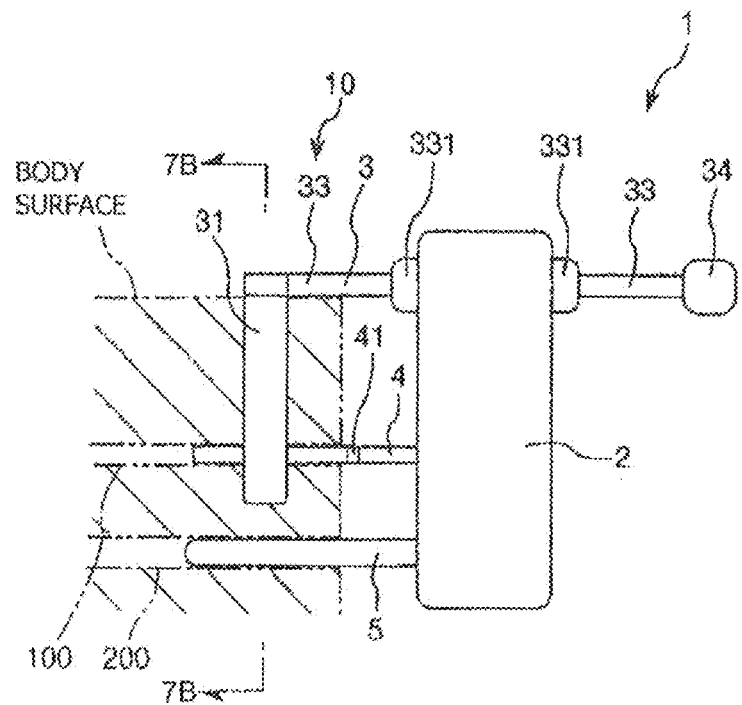
FIGS. 7(a) and 7(b) are views illustrating an operation procedure of the puncture apparatus depicted in FIG. 1 with FIG. 7(b) taken along the section line 7B-7B in FIG. 7(a).
Figure 7B:
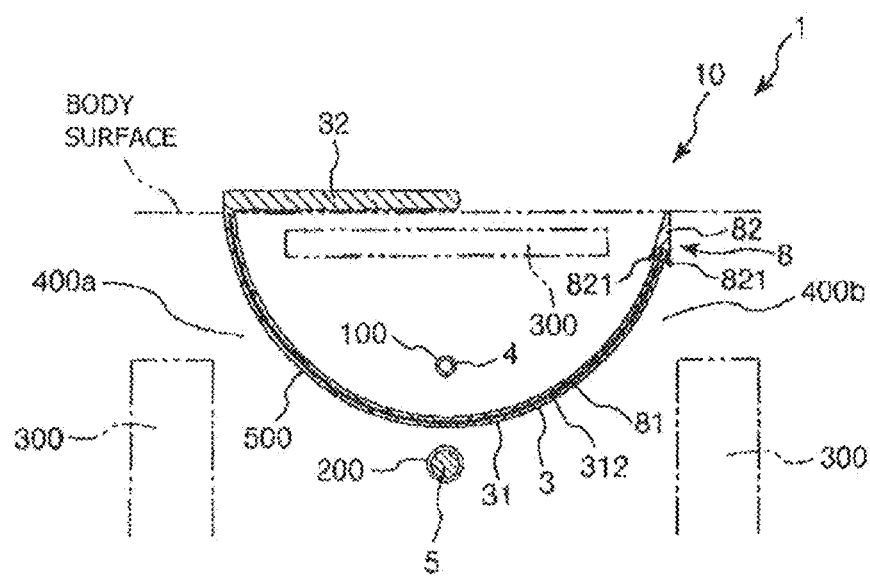
Figure 8A:
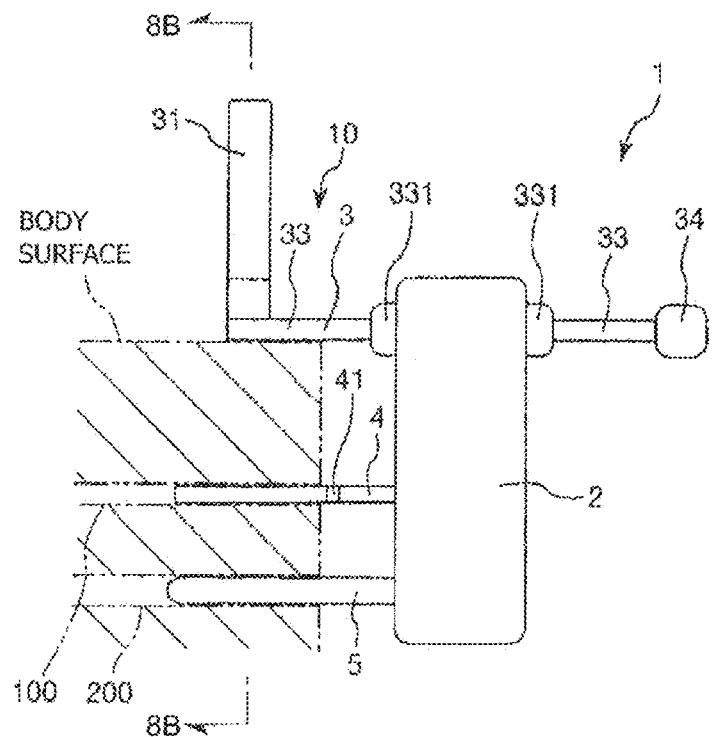
FIGS. 8(a) and 8(b) are views illustrating an operation procedure of the puncture apparatus depicted in FIG. 1 with FIG. 8(b) taken along the section line 8B-8B in FIG. 8(a).
Figure 8B:
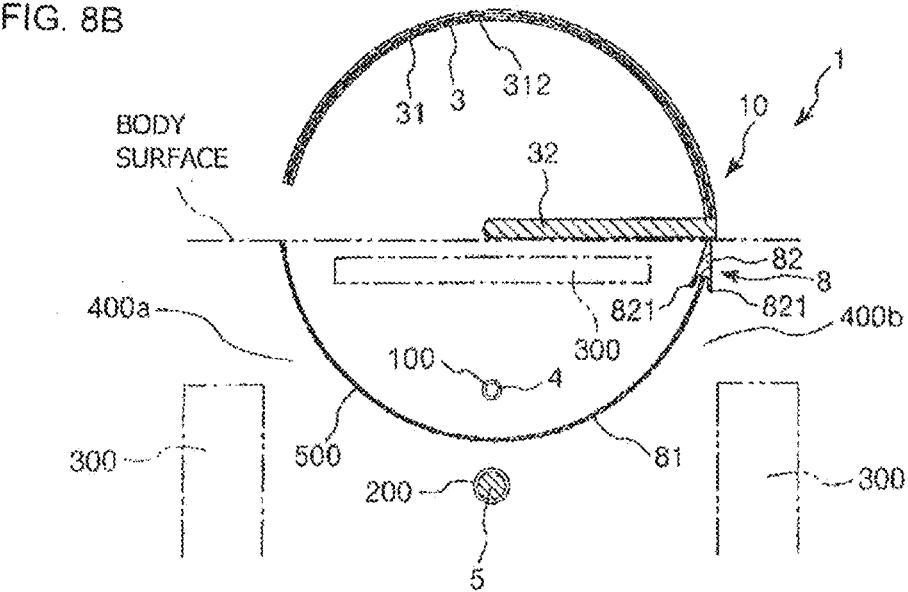
Figure 9:
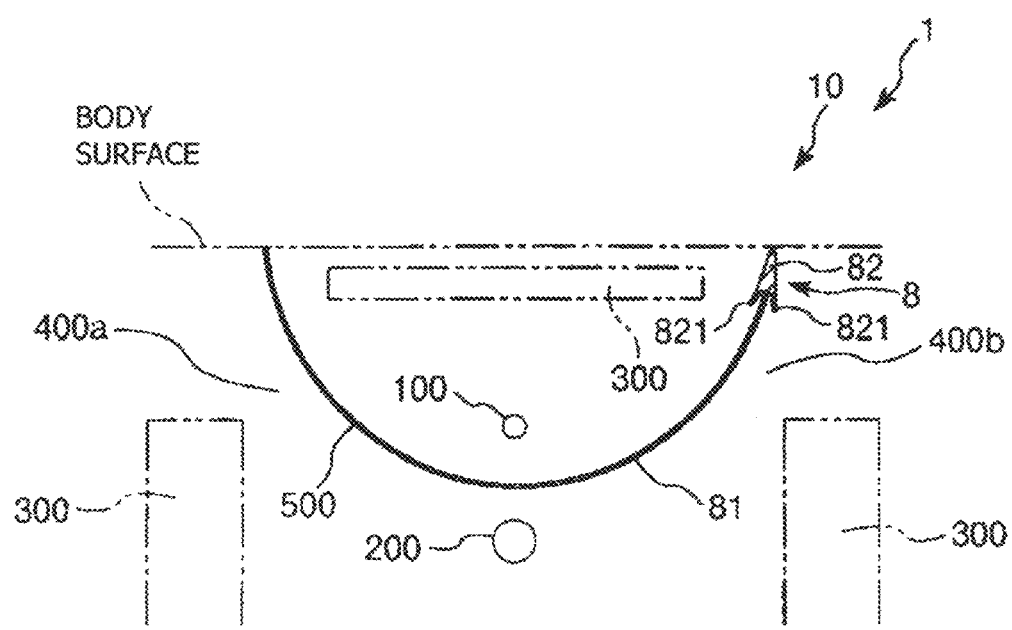
FIG. 9 is a view illustrating an operation procedure of the puncture apparatus depicted in FIG. 1 taken along the section line 5B-5B in FIG. 5(a).

As depicted in FIGS. 1 to 3, the puncture apparatus 1 can include a puncture device 10 for puncturing a biological tissue, a urethral-insertion member 4 of a longitudinal shape for being inserted into a urethra, a vaginal-insertion member 5 of a longitudinal shape for being inserted into a vagina, and a supporting member (restriction means) 2 for supporting the urethral-insertion member 4, the vaginal-insertion member 5 and a puncture member 3 (hereinafter described) of the puncture device 10.

The puncture device 10 can include a puncture needle 31 for puncturing a biological tissue, a puncture member 3 having a shaft portion 33 and a connection portion 32 for connecting the puncture needle 31 and the shaft portion 33 to each other, and an implant (or indwelling article) assembly 8 having a needle tip portion 82 positioned at the distal end of the puncture needle 31 and configured to puncture a biological tissue and a biological tissue supporting implant (or indwelling article) 81. The puncture needle 31 has a form of a pipe and has a hollow portion 312, and the biological tissue supporting implant 81 is accommodated in the hollow portion 312.

The implant assembly 8 has the biological tissue supporting implant 81 in the form of a belt for attaching to a biological tissue, and the needle tip portion 82 fixed to a distal end portion of the biological tissue supporting implant 81 for puncturing a biological tissue. The biological tissue supporting implant 81 of the implant assembly 8 is called a "sling." In the present exemplary embodiment, the biological tissue supporting implant 81 and the needle tip portion 82 can be buried into a living body.

The biological tissue supporting implant 81 can have a net-like form and can be configured, for example, as an article braided in a net-like form (lattice form) of crossing linear bodies, for example, as a braided body having a net-like form. The linear bodies may be, for example, those having a circular transverse sectional shape, those having a flattened transverse sectional shape, for example, those of a belt-like form (ribbon form).

It can be appreciated that the biological tissue supporting implant 81 is not limited to that of the net-like form described above.

In accordance with an exemplary embodiment, the needle tip portion 82 has, at an apex portion of the needle tip portion 82, a rounded and non-sharp needle tip for puncturing a biological tissue. Consequently, when the needle tip portion 82 is buried in a living body, the biological tissue can be prevented from being damaged. The needle tip portion 82 can be fixed at a proximal end portion of needle tip portion 82 to the distal end portion of the biological tissue supporting implant 81.

Further, a pair of protrusions 821 can be formed at an outer circumferential portion of the proximal end portion of the needle tip portion 82 such that they protrude toward a direction of the proximal end. The protrusions 821 are arranged in an opposing relationship to each other across the center axis of the puncture needle 31. Further, the protrusions 821 are spaced from each other by a greater amount in the proximal end side than in the distal end side. Consequently, the needle tip portion 82 can be prevented from returning in the opposite direction to the puncturing direction of the needle tip portion 82, and an anchor effect can be obtained.

The constituent materials of the needle tip portion 82 and the biological tissue supporting implant 81 are not limited, and can be configured using, for example, various resin materials having biocompatibility.

In the implant assembly 8, the biological tissue supporting implant 81 is accommodated in the hollow portion 312 of the puncture needle 31, and the needle tip portion 82 is held removably, for example, detachably, at a distal end portion of the puncture needle 31.

In the present exemplary embodiment, the urethral-insertion member 4 is firmly fixed to the supporting member 2.

The urethral-insertion member 4 has a straight tubular shape made of non-flexible hard material, and an opening at the proximal end of urethral-insertion member 4 is open at the proximal end face of the supporting member 2. Into the urethral-insertion member 4, various kinds of elongated medical tools can be inserted, for example, a balloon catheter 11, which can include an expandable and contractible balloon 111 at the distal end portion of balloon catheter 11 as depicted in FIG. 4. In FIG. 4, the balloon 111 in a contracted state is indicated by a solid line, and the balloon 111 in an expanded state is indicated by an alternate long and two-short dashes line.

The balloon 111 of the balloon catheter 11 can function as a restriction unit for restricting the position of the urethral-insertion member 4 in the axial direction (longitudinal direction) inside the urethra. For example, when the puncture apparatus 1 is to be used, the balloon 111 is inserted into the bladder of a patient, and the positional relation in the axial direction between the balloon catheter 11 and the urethral-insertion member 4 is fixed. Besides, the balloon 111 is caught by the bladder neck in a state in which the balloon 111 is expanded, and consequently, the position of the urethral-insertion member 4 with respect to the bladder and the urethra is fixed.

In accordance with an exemplary embodiment, a balloon expanding tool such as, for example, a syringe (not shown) can be connected to a port (not shown), which can communicate with a lumen (not shown) which communicates with the balloon 111 of the balloon catheter 11. Operating fluid supplied from the balloon expanding tool can then be sent into or extracted from the inside of the balloon 111 thorough the aforementioned lumen to carry out expansion and contraction of the balloon 111. As the operating fluid for the expansion of the balloon, liquids such as, for example, physiological salt solution, or a gas can be used.

In accordance with an exemplary embodiment, the balloon catheter 11 can be used for the urination of the patient when the puncture apparatus 1 is being used.

A marker 41 can be provided at an outer circumferential portion of the urethral-insertion member 4. The marker 41 is arranged such that the marker 41 is positioned at the urethral orifice when the urethral-insertion member 4 is inserted into the urethra and the distal end portion of the urethral-insertion member 4 is positioned just in front of the bladder.

In the present exemplary embodiment, the vaginal-insertion member 5 is firmly fixed to the supporting member 2. The vaginal-insertion member 5 may otherwise be removably provided on the supporting member 2. The vaginal-insertion member 5 has a form of a straight bar. Further, the distal end portion of the vaginal-insertion member 5 is rounded. Consequently, the vaginal-insertion member 5 can be smoothly inserted into the vagina.

Further, the vaginal-insertion member 5 is arranged in a spaced relationship by a predetermined distance from the urethral-insertion member 4 below the urethral-insertion member 4 such that the axial line of the vaginal-insertion member 5 and the axial line of the urethral-insertion member 4 extend in parallel to each other.

The constituent materials of the vaginal-insertion member 5, the urethral-insertion member 4 and the supporting member 2 are not limited, and, for example, various kinds of resin materials can be used.

The puncture member 3 of the puncture device 10 is installed, at the shaft portion 33 of puncture device 10 which serves as a rotational shaft, for rotational movement on the supporting member 2.

Further, the shaft portion 33 is arranged in a spaced relationship by a predetermined distance from the urethral-insertion member 4 above the urethral-insertion member 4 such that the axial line of shaft portion 33 and the axial line of the urethral-insertion member 4 extend in parallel to each other. Further, as viewed from an axial direction of the shaft portion 33, the shaft portion 33, urethral-insertion member 4 and vaginal insertion member 5 are arranged on a straight line.

The shaft portion 33 passes through the supporting member 2 in the leftward and rightward direction in FIG. 1. On the distal end and the proximal end of the shaft portion 33, a first flange 331 and a second flange 332 are formed, respectively, with the supporting member 2 interposed between the first and second flanges 331, 332. The movement of the shaft portion 33 in the axial direction with respect to the supporting member 2 is blocked by the flanges 331 and 332.

The puncture needle 31 can have a form of a pipe and has a hollow portion 312. The hollow portion 312 is open at the distal end and closed at the proximal end of the puncture needle 31. Further, the puncture needle 31 can have a flattened shape as viewed in the longitudinal direction of puncture needle 31. In accordance with an exemplary embodiment, the transverse sectional shape of the puncture needle 31 corresponds to the transverse sectional shape of the biological tissue supporting implant 81. Consequently, a puncture hole 500 of a shape corresponding to that of the biological tissue supporting implant 81 can be formed in a patient, and the implant assembly 8 can be buried more readily and appropriately.

Further, the puncture needle 31 is curved in an arc centered at the shaft portion 33. Further, as shown in FIG. 1, the axial line of the puncture needle 31 and the axial line of the shaft portion 33 cross orthogonally with each other. Consequently, when the puncture member 3 is rotationally moved, the needle tip of the puncture needle 31 moves along the arc described above in a plane perpendicular to the axial line of the shaft portion 33, for example, in a plane having a normal line at the axial line.

Further, while, in the present exemplary embodiment, the distal end of the puncture needle 31 is directed in a counterclockwise direction as shown in FIG. 2, the direction of the distal end of the puncture needle 31 is not limited to this and the distal end of the puncture needle 31 may be directed in a clockwise direction in FIG. 2.

Further, in the present exemplary embodiment, the puncture needle 31 is arranged at the proximal end side with respect to a distal end portion of the urethral-insertion member 4 in the axial direction of the urethral-insertion member 4.

In accordance with an exemplary embodiment, the puncture needle 31 may be arranged at a position same as that of a distal end portion of the urethral-insertion member 4 in the axial direction of the urethral-insertion member 4 or may be arranged at the distal end side with respect to the distal end portion of the urethral-insertion member 4.

In accordance with an exemplary embodiment, the supporting member 2 can restrict the positional relationship between the puncture device 10 and the urethral-insertion member 4 so that, when the puncture device 10 is rotationally moved and punctuates a biological tissue, the needle tip of the needle tip portion 82 can pass at the farther-position side from the center 311 of the puncture needle 31 than the urethral-insertion member 4 or an extension line of the urethral-insertion member 4, for example, below the urethral-insertion member 4 or the extension line of the urethral-insertion member 4. In accordance with an exemplary embodiment, the center 311 of the puncture needle 31 is the center of the arc of the puncture needle 31. Thus, the center 311 of the puncture needle 31 is the center of the rotational movement of the puncture needle 31 (puncture device 10).

Further, the supporting member 2 can restrict the positional relationship between the puncture device 10 and the vaginal insertion member 5 so that, when the puncture device 10 is rotationally moved and punctures a living body, the needle tip of the needle tip portion 82 may not collide with the vaginal insertion member 5 and an extension line of the vaginal insertion member 5.

In accordance with an exemplary embodiment, the supporting member 2 can restrict the positional relationship among the puncture device 10, urethral-insertion member 4 and vaginal insertion member 5 so that, when the puncture device 10 is rotationally moved and punctures a living body, the needle tip of the needle tip portion 82 can pass between the urethral-insertion member 4 or the extension line of the urethral-insertion member 4 and the vaginal insertion member 5 or the extension line of the vaginal insertion member 5.

Consequently, the puncture device 10 can puncture a biological tissue avoiding the urethra and the vaginal wall, and the puncture device 10 can be prevented from puncturing the urethra and from puncturing the vaginal wall.

In addition, since the trajectory of the needle tip of the needle tip portion 82 of the puncture device 10 is determined, the puncture device 10 can help prevent the fingertip of the operator from being punctured by the puncture device 10.

Further, although the center angle of the arc of the puncture needle 31 is not restricted particularly but is set suitably in response to various conditions, the center angle is set such that, when a biological tissue is punctured by the puncture device 10, the needle tip portion 82 of the puncture device 10 can enter into the body from the body surface at one side of a patient, passes below the urethra and can move to a position in the proximity of the body surface at another side of the patient.

In accordance with an exemplary embodiment, the center angle $\theta 1$ of the arc of the puncture needle 31 and the needle tip portion 82, for example, is about 150 degrees to 270 degrees, for example, about 170 degrees to 250 degrees, and for example, about 190 degrees to 230 degrees.

Consequently, when a biological tissue is punctured by the puncture device 10, the needle tip portion 82 can enter into the body from the body surface at one side of the patient, pass below the urethra and be positioned in the proximity of the body surface at the other side without penetrating the body surface at the other side.

Further, a grip unit 34 can be provided as an operation unit for operating the puncture device 10 to move rotationally is provided at a proximal end portion of the shaft portion 33. The shape of the grip unit 34 in the present exemplary embodiment can have a form of a rectangular solid. When the puncture device 10 is to be moved rotationally, the grip unit 34 can be gripped by the fingers of a hand and can be moved rotationally in a predetermined direction. The shape of the grip unit 34 is not to be limited to the disclosed exemplary embodiment.

The constituent material of the puncture member 3 is not limited, and such various metal materials, for example, as stainless steel, aluminum or aluminum alloy and titanium or titanium alloy can be used as the constituent material of the puncture member 3.

In accordance with an exemplary embodiment, an operation procedure of the puncture apparatus 1, for example, a procedure when the implant assembly 8 is buried into a living body, is described.

First, the puncture apparatus 1 is mounted on a patient as depicted in FIGS. 5(*a*) and 5(*b*). In particular, the urethral-insertion member 4 of the puncture apparatus 1 is inserted into the urethra 100 of the patient and the vaginal-insertion member 5 is inserted into the vagina 200 of the patient. At the time, the insertion is carried out such that the marker 41 is positioned at the urethral orifice or on the front side of the urethral orifice. Consequently, the distal end portion of the urethral-insertion member 4 can be arranged on the front side of the bladder.

The grip unit 34 is then grasped as depicted in FIGS. 6(*a*), 6(*b*), 7(*a*), and 7(*b*) and rotationally moves the puncture device 10 counterclockwise as shown in FIGS. 6(*b*) and 7(*b*).

Consequently, the needle tip of the needle tip portion 82 of the puncture device 10 moves counterclockwise in FIGS. 6(*b*) and 7(*b*) along the arc of needle tip portion 82; punctures the body surface at an inguinal region of the patient on the left side in FIGS. 6(*b*) and 7(*b*) or at a region in the vicinity of the same; enters into the body; passes an obturator foramen 400*a* of a pelvis 300; passes below the urethra 100, for example, passes between the urethra 100 and the vagina 200; passes an obturator foramen 400*b* of the pelvis 300; and moves to the proximity of an inguinal region on the right side in FIGS. 6(*b*) and 7(*b*) or at a region in the proximity of the inguinal region. In accordance with an exemplary embodiment, the needle tip of the needle tip portion 82 does not penetrate the body surface at the inguinal region on the right side or at a region in the proximity of the inguinal region. Consequently, in the patient, a puncture hole 500 is formed which extends from the body surface at the inguinal region at the left side in FIGS. 6(*b*) and 7(*b*) or at a region in the proximity of the inguinal region past the obturator foramen 400*a*, a region between the urethra 100 and the vagina 200 and the obturator foramen 400*b* to a position in the proximity of the body surface at the inguinal region at the right side in FIGS. 6(*b*) and 7(*b*) or at a region in the proximity of the inguinal region.

As depicted in FIG. 8, the grip unit 34 is then grasped and the puncture device 10 is rotationally moved clockwise in FIG. 8.

Thereupon, the implant assembly 8 can be prevented from returning in the opposite direction to the puncturing direction by the protrusions 821 of the needle tip portion 82. Further, the distal end of the puncture needle 31 can move in the clockwise direction in FIG. 8 along the arc of the puncture needle 31; pass through the obturator foramen 400*b* of the pelvis 300; pass below the urethra 100; for example; pass a location between the urethra 100 and the vagina 200; pass through the obturator foramen 400*a* of the pelvis 300; and come out to the outside of the body from the body surface at the inguinal region at the left side in FIG. 8 or at a region in the proximity of the inguinal region. The puncture needle 31 can then be pulled out to the outside of the body. The implant assembly 8, for example, the biological tissue supporting implant 81, can be buried into the living body in such a manner as described above.

The puncture apparatus 1 is then removed from the patient. For example, the urethral-insertion member 4 can be pulled out from within the urethra 100 and the vaginal insertion member 5 is pulled out from within the vagina 200 of the patient. Then, a predetermined treatment can be carried out, thereby ending the manual procedure.

As described above, with the puncture apparatus 1, when the biological tissue supporting implant 81 is to be indwelled, the indwelling operation can be carried out only by a low invasive manual procedure such as puncturing of the puncture device 10. Since it is not necessary to carry out a high invasive incision or the like, the burden on the patient is relatively light and the safety of the patient is relatively high.

Further, the puncture device 10 can puncture the living body and avoid the urethra and the vaginal wall, and help prevent the puncture device 10 from puncturing the urethra and puncturing the vaginal wall. The puncture device 10 can also help prevent the fingertip of the operator from being punctured by the puncture device 10. Therefore, relative safety can be achieved.

Furthermore, the puncture device 10 can help prevent situations such as in a conventional case in which the vagina is incised that the biological tissue supporting implant 81 is exposed to the inside of the vagina through a wound caused by the incision or complications, for example, an infection from the wound. Therefore, the biological tissue supporting implant 81 can be buried in very relatively high safety and with relative certainty.

Further, since the biological tissue supporting implant 81 is accommodated in the hollow portion 312 of the puncture needle 31, the biological tissue supporting implant 81 can readily be buried.

In accordance with an exemplary embodiment, although one end portion of the puncture hole formed in the patient by the puncture device does not penetrate the body surface, the puncture hole is not limited to this and may be a through-hole.

Further, the urethral-insertion member is not limited to that of a tubular shape, and may be, for example, a solid member or may be a hollow member, which is closed at one or both of the distal end and/or the proximal end portions of the urethral-insertion member.

Further, at the distal end portion of the urethral-insertion member, an expandable and contractible balloon may be provided as a restriction unit for restricting the position of the urethral-insertion member in the axial direction inside the urethra.

Further, while the puncture needle of the puncture device in the present exemplary embodiment is curved in an arc over an overall extent of puncture needle, the puncture needle is not limited to this and only a part of the puncture needle may have an arcuately curved portion. For example, in accordance with an exemplary embodiment, at least a part of the puncture needle can have an arcuately curved portion.

Further, the puncture needle may have a curved portion at least at part of the puncture needle, and, for example, may be curved in an elliptical arc over an overall extent of puncture needle or only at part of the puncture needle may have a portion curved in an elliptical arc. In other words, at least at part of the puncture needle may have a portion curved in an elliptical arc.

FIGS. 10-19 depict a second exemplary embodiment of the puncture apparatus of the present disclosure. In FIG. 13(b), FIG. 14(b), FIG. 15(b) and FIGS. 16 to 19, slanting lines for a living body is omitted to be easily viewable. In the following description in FIG. 10, FIG. 13(a), FIG. 14(a), and FIG. 15(a), the left side is the "distal end" and the right side is "proximal end."

In the following, the second exemplary embodiment is described principally in regard to differences from the first exemplary embodiment described hereinabove, while the description of similar matters is omitted.

Figure 10:
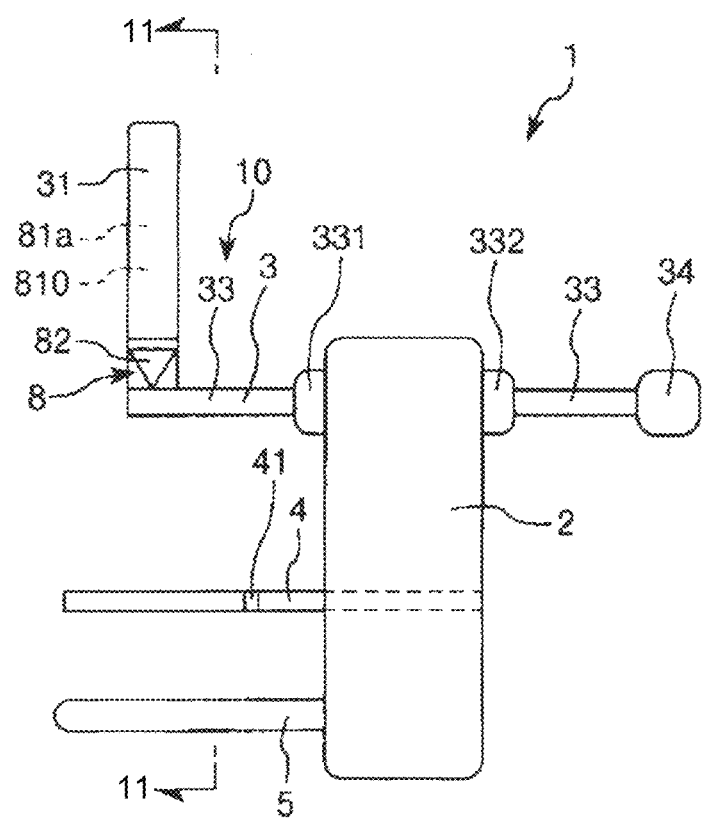
FIG. 10 is a side elevational view depicting a second exemplary embodiment of the puncture apparatus of the present disclosure.
Figure 12:
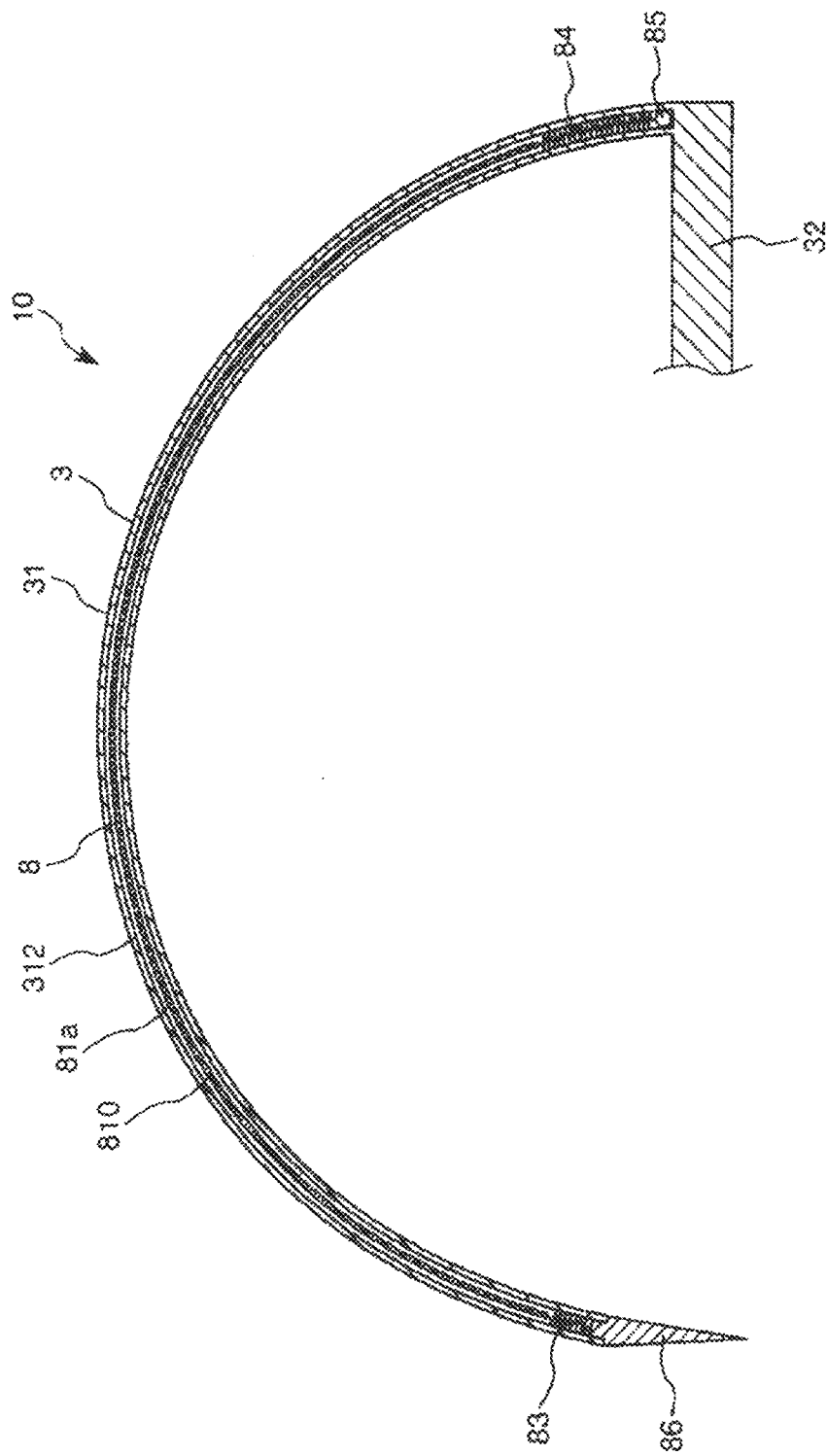
FIG. 12 is a cross sectional view of a puncture device of the puncture apparatus depicted in FIG. 10.
Figure 13A:
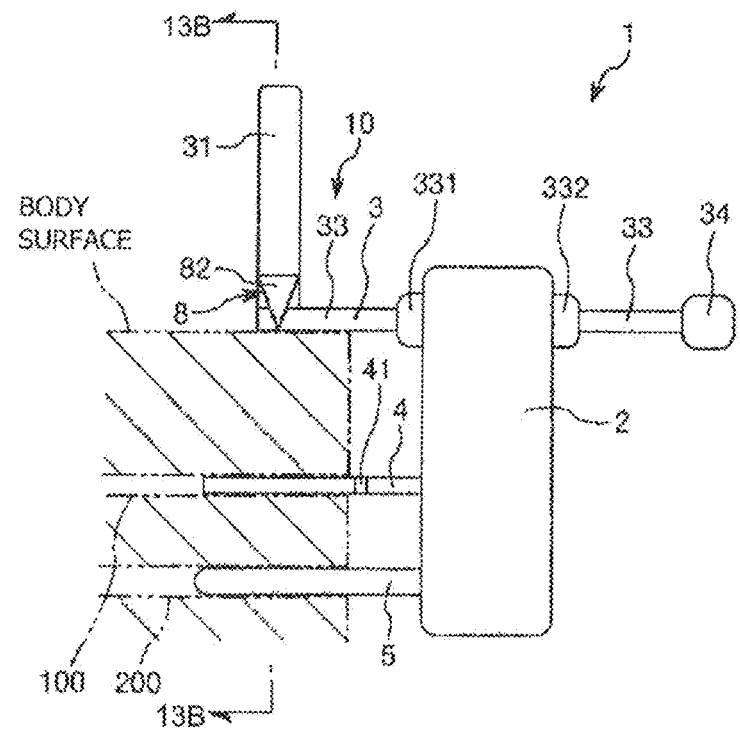
FIGS. 13(a) and 13(b) are views illustrating an operation procedure of the puncture apparatus depicted in FIG. 10 with FIG. 13(b) taken along the section line 13B-13B in FIG. 13(a).
Figure 13B:
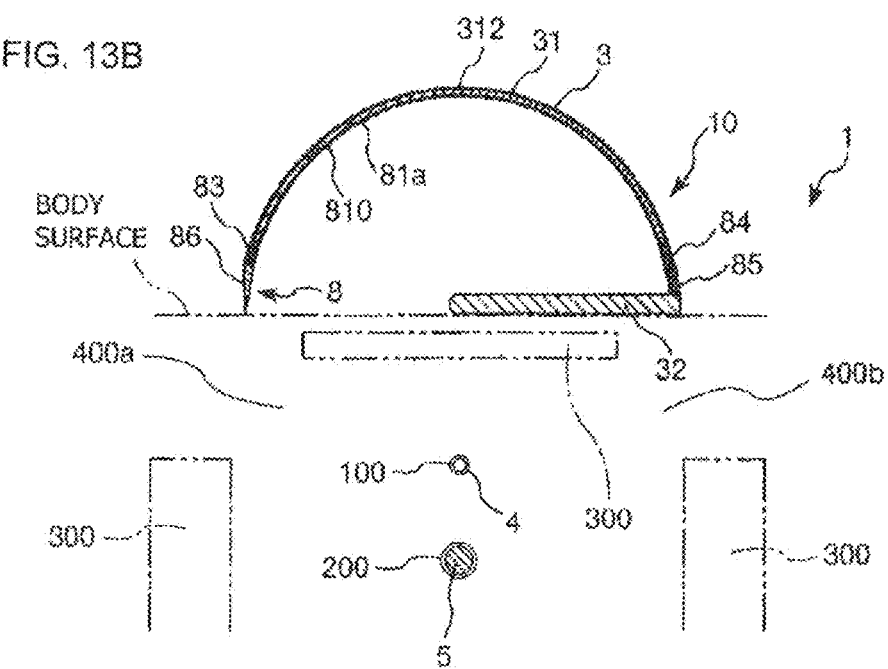
Figure 14A:
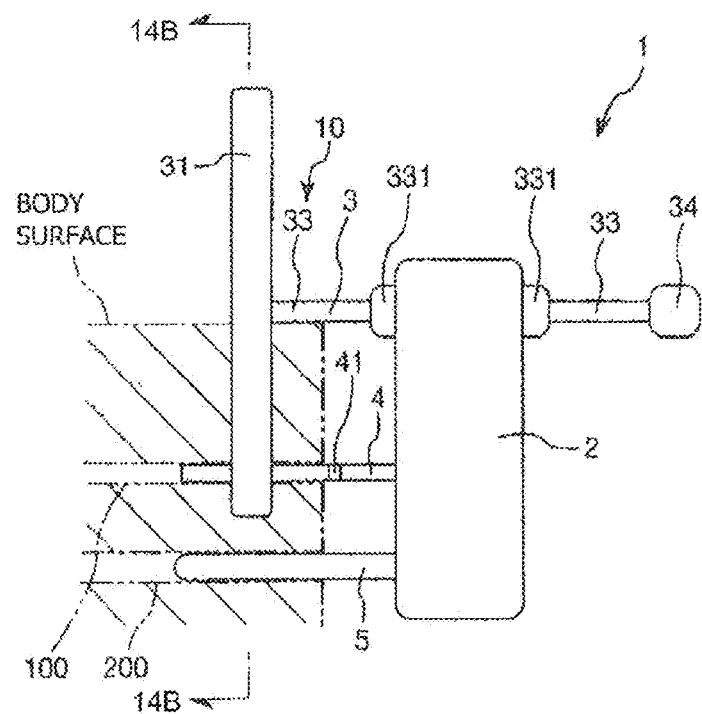
FIGS. 14(a) and 14(b) are views illustrating an operation procedure of the puncture apparatus depicted in FIG. 10 with FIG. 14(b) taken along the section line 14B-14B in FIG. 14(a).
Figure 14B:
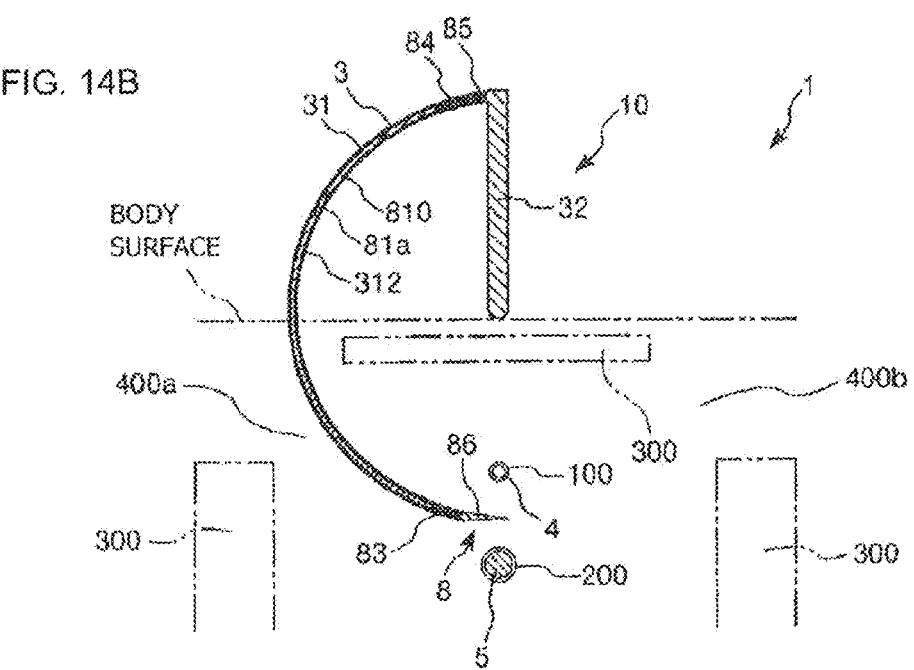
Figure 15A:
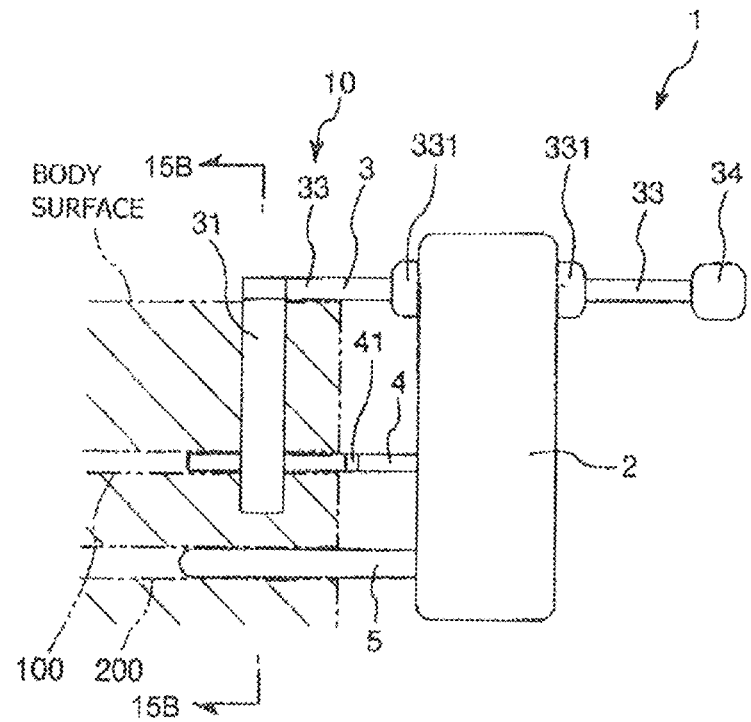
FIGS. 15(a) and 15(b) are views illustrating an operation procedure of the puncture apparatus depicted in FIG. 10 with FIG. 15(b) taken along the section line 15B-15B in FIG. 15(a).
Figure 15B:
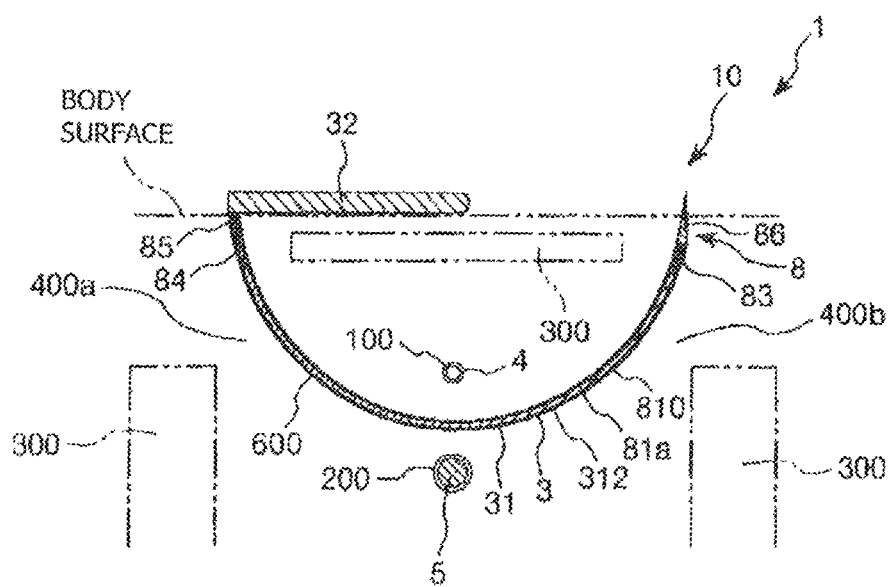

As depicted in FIGS. 10 to 12, in the puncture apparatus 1 of the second embodiment, the biological tissue supporting implant 81a of the implant assembly 8 can include an implant (or indwelling article) main body 810, a proximal end of a string (first string member) 83, which is connected to the distal end of the implant main body 810, a distal end of a string (second string member) 84, which is connected to the proximal end of the implant main body 810, and a holding member 85, which is connected to the proximal end of the string 84. For example, the string 83 can be fixed at a proximal end portion of string 83 to a distal end portion of the implant main body 810, and the string 84 can be fixed at a distal end portion of string 84 to a proximal end portion of the implant main body 810. Further, the holding member 85 can be fixed to a proximal end portion of string 84 and is held removably, for example, detachably, on the hollow portion 312 at a proximal end portion of the puncture needle 31. In accordance with an exemplary embodiment, the implant main body 810 is similar to the biological tissue supporting implant 81 in the first exemplary embodiment.

In accordance with an exemplary embodiment, the holding member 85 in the present exemplary embodiment can have a spherical shape. The shape of the holding member 85 is not limited to a spherical shape and can have other shapes.

Further, the constituent materials of the strings 83 and 84 are not limited and can be configured, for example, using various resin materials and/or fiber materials. In addition, the constituent material of the holding member 85 is not limited, and can be configured, for example, using various resin materials.

Further, a needle tip portion 86 of the implant assembly 8 has a sharp needle tip at the distal end of the needle tip portion 86. The needle tip portion 86 can be fixed to a distal end portion of the string 83.

In the present exemplary embodiment, the needle tip portion 86 and the holding member 85 of the implant assembly 8 are not buried in a living body, but the implant main body 810 of the biological tissue supporting implant 81a and part of the strings 83 and 84 are buried in a living body.

Further, the center angle of the arc of the puncture needle 31 is not limited, and can be set suitably in response to various conditions. However, the center angle is set such that, when the puncture device 10 punctures a biological tissue, the needle tip portion 86 of the puncture device 10 can enter into the body from the body surface at one side of the patient, pass below the urethra and protrude to the outside of the body from the body surface at the other side.

For example, the center angle 82 of the arc of the puncture needle 31 and the needle tip portion 86 is about 150 degrees to 270 degrees, for example, about 170 degrees to 250 degrees, and for example, about 190 degrees to 230 degrees.

Consequently, when the puncture device 10 punctures a biological tissue, the needle tip portion 86 can enter into the body from the body surface at one side of the patient, pass below the urethra and protrude to the outside of the body from the body surface at the other side with certainty.

In accordance with an exemplary embodiment, an operation procedure of the puncture apparatus 1, for example, a procedure when the implant main body 810 of the implant assembly 8 is buried into a living body, is described.

First, the puncture apparatus 1 is mounted on a patient as depicted in FIG. 13. In particular, the urethral-insertion member 4 of the puncture apparatus 1 is inserted into the urethra 100 of the patient and the vaginal-insertion member 5 is inserted into the vagina 200 of the patient. At the time, the insertion is carried out such that the marker 41 is positioned at the urethral orifice or on the front side of the urethral orifice. Consequently, the distal end portion of the urethral-insertion member 4 can be arranged on the front side of the bladder.

The grip unit 34 is then grasped as depicted in FIGS. 14(*a*) and 15(*a*), and rotationally moves the puncture device 10 counterclockwise as shown in FIGS. 14(*b*) and 15(*b*).

Consequently, the needle tip of the needle tip portion 86 of the puncture device 10 moves counterclockwise in FIGS. 14(*b*) and 15(*b*) along the arc of the needle tip portion 86; punctures the body surface at an inguinal region of the patient on the left side in FIGS. 15(*b*) and 16(*b*) or at a region in the vicinity of the same; enters into the body; passes an obturator foramen 400a of a pelvis 300; passes below the urethra 100, for example, passes between the urethra 100 and the vagina 200; passes an obturator foramen 400b of the pelvis 300; and protrudes to the outside of the body from the body surface at the inguinal region at the right side in FIG. 14(*b*) and FIG. 15(*b*) or at a region in the proximity of the inguinal region. Consequently, in the patient, a puncture hole 600 is formed which extends from the body surface at an inguinal region on the left side in FIGS. 14(*b*) and 15(*b*) or at a region in the vicinity of the same to the body surface at an inguinal region on the right side in FIGS. 14(*b*) and 15(*b*) or at a region in the vicinity of the same while passing through the obturator foramen 400a, between the urethra 100 and the vagina 200 and through the obturator foramen 400b.

Figure 16:
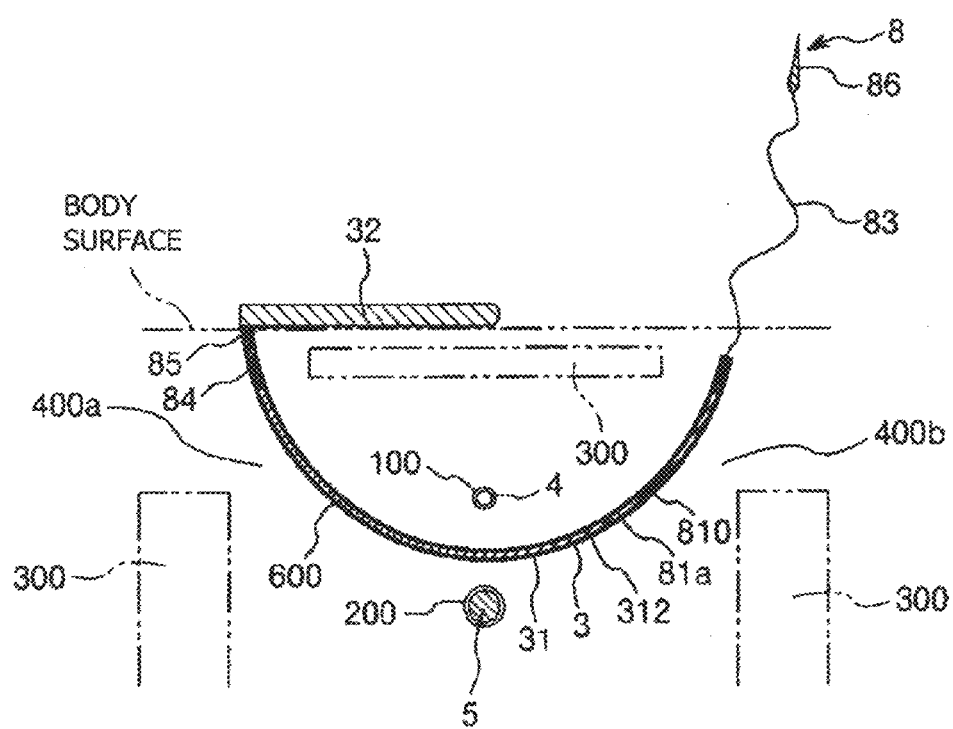
FIG. 16 is a view illustrating an operation procedure of the puncture apparatus depicted in FIG. 10.
Figure 17:
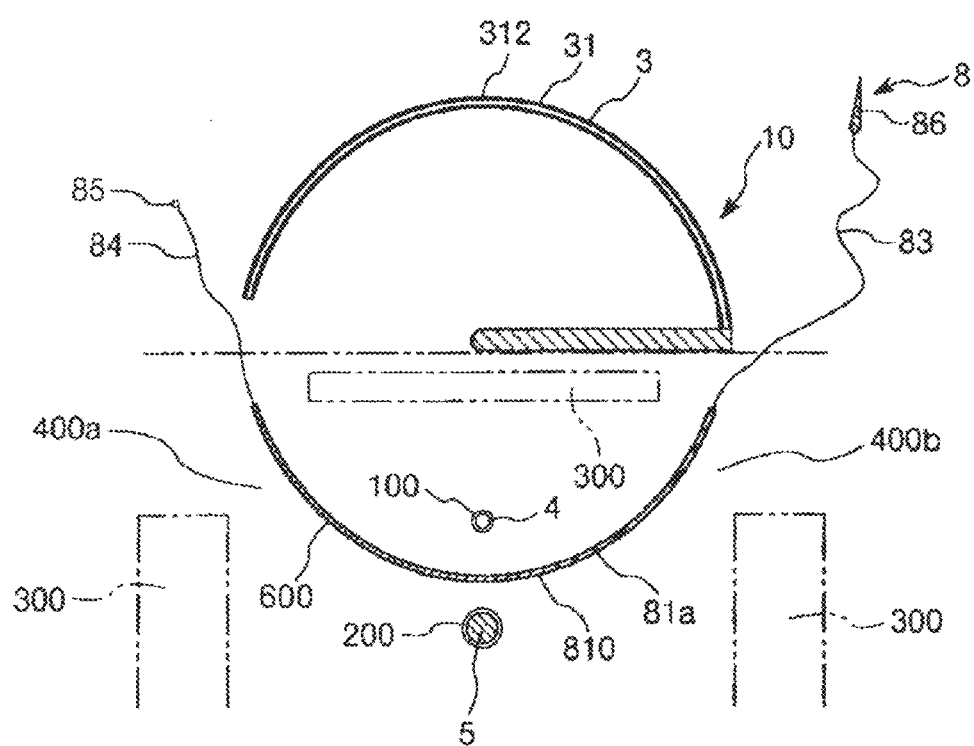
FIG. 17 is a view illustrating an operation procedure of the puncture apparatus depicted in FIG. 10.

The needle tip portion 86 is then removed from the distal end portion of the puncture needle 31 as depicted in FIG. 16, and the grip unit 34 is grasped as depicted in FIG. 17 to rotate the puncture device 10 clockwise as shown in FIG. 8.

In accordance with an exemplary embodiment, the distal end of the puncture needle 31 moves clockwise in FIG. 17 along the arc of the puncture needle 31; passes through the obturator foramen 400b of the pelvis 300; passes below the urethra 100, for example, passes between the urethra 100 and the vagina 200; passes through the obturator foramen 400a of the pelvis 300; and goes out to the outside of the body from the body surface at an inguinal region at the left side in FIG. 17 or at a region in the proximity of the same. That is, the puncture needle 31 is removed to the outside of the body.

The holding member 85 is then removed from the distal end of the hollow portion 312 of the puncture needle 31. Further, the puncture apparatus 1 is removed from the patient. In particular, the urethral-insertion member 4 is pulled out from within the urethra 100, and the vaginal insertion member 5 is pulled out from within the vagina 200 of the patient.

Figure 18:
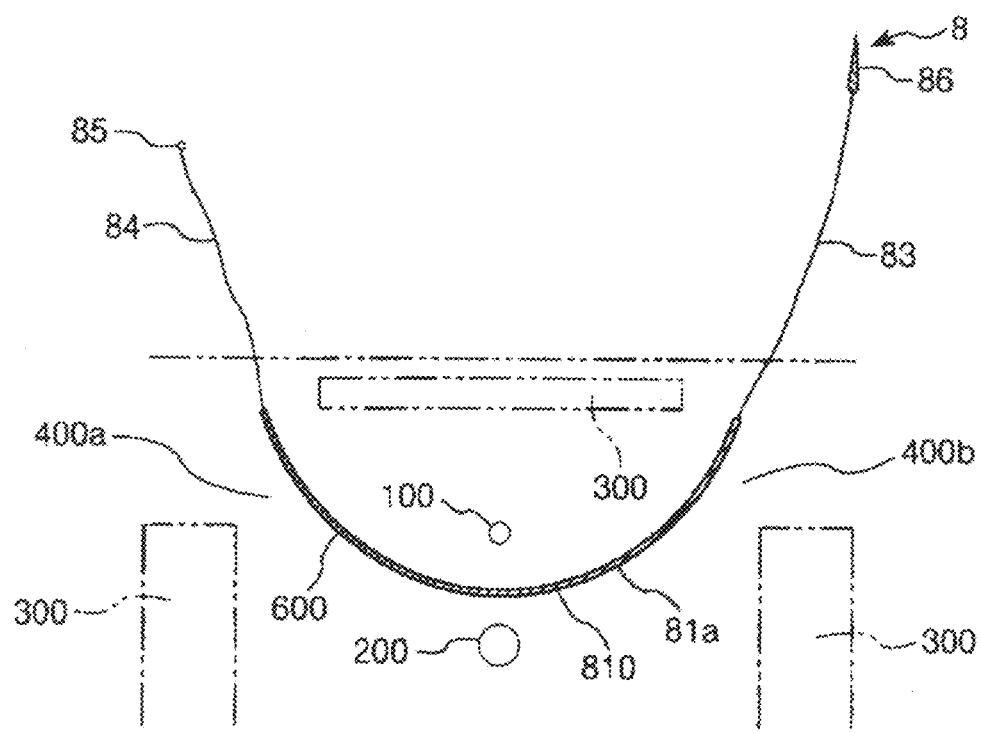
FIG. 18 is a view illustrating an operation procedure of the puncture apparatus depicted in FIG. 10.
Figure 19:
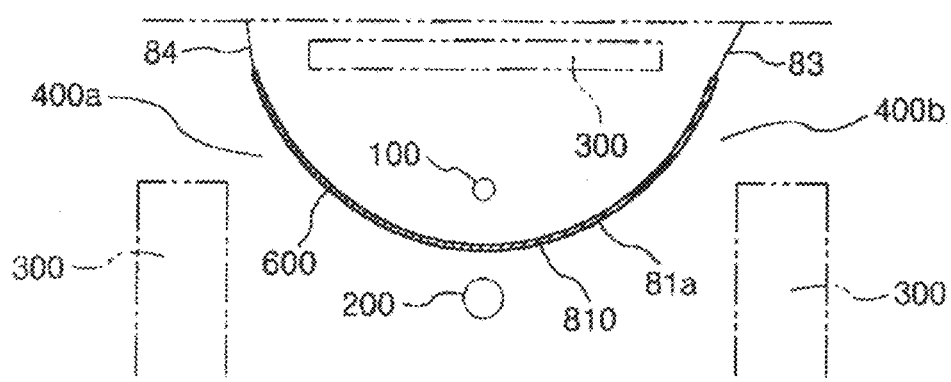
FIG. 19 is a view illustrating an operation procedure of the puncture apparatus depicted in FIG. 10.

The strings 83 and 84 are then pulled individually by predetermined forces as depicted in FIG. 18 to adjust the position of the implant main body 810 with respect to the urethra 100, and unnecessary portions of the strings 83 and 84 can be cut away. A predetermined treatment can then be carried out, thereby ending the manual procedure. The implant main body 810 is buried into the biological tissue in this manner.

With the present puncture apparatus 1, similar effects to those by the first embodiment described hereinabove are achieved.

In accordance with an exemplary embodiment, while the needle tip portion in the present exemplary embodiment is fixed to a distal end portion of a string, the fixation of the needle tip portion is not limited to this, and the needle tip portion may be held removably, for example, detachably, on a string.

Figure 20:
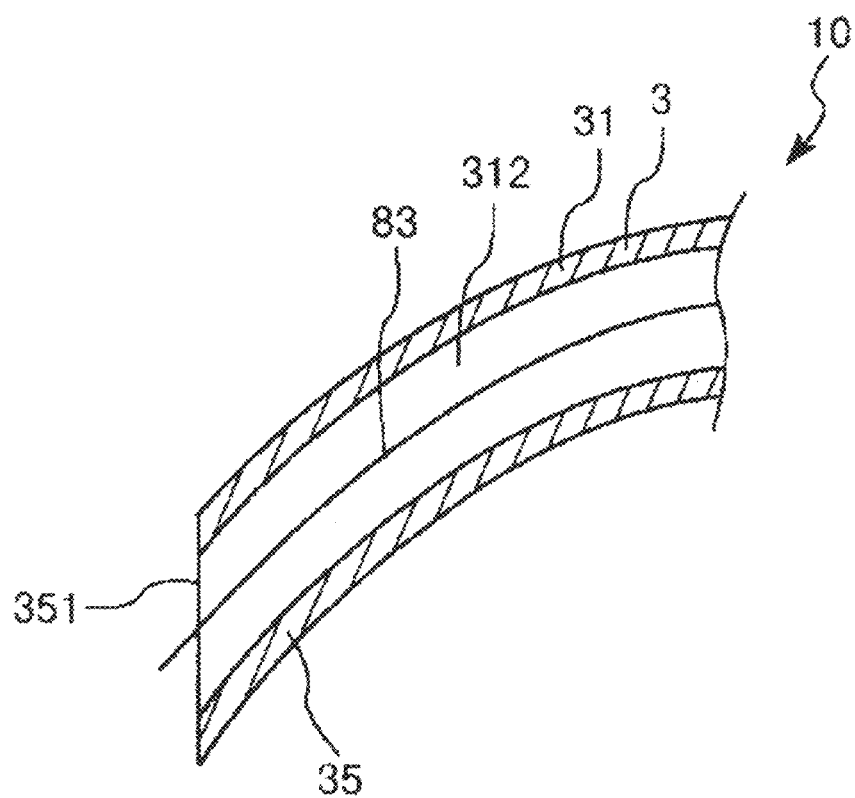
FIG. 20 is a cross sectional view depicting a puncture device according to a third exemplary embodiment of the puncture apparatus of the present disclosure.

FIG. 20 is a cross sectional view depicting a puncture device according to a third embodiment of the puncture apparatus of the present disclosure.

In the following, the third embodiment is described principally in regard to differences from the second exemplary embodiment described hereinabove, while the description of similar items is omitted.

As depicted in FIG. 20, in the puncture apparatus 1 of the third exemplary embodiment, the puncture needle 31 of the puncture device 10 has a needle tip portion 35 at a distal end portion of the puncture needle 31. In accordance with an exemplary embodiment, the needle tip portion 35 can be fixed to or integrated with the distal end portion of the puncture needle 31. Further, the needle tip portion 35 has a sharp needle tip at the distal end of the needled tip portion 35. Further, the hollow portion 312 can be open at both of the distal end and the proximal end of the puncture needle 31. Further, the puncture device 10 has a pusher not depicted for pushing the string 83 of the biological tissue supporting implant 81a in a direction toward the distal end.

In the exemplary puncture apparatus 1, when it is to be used, the pusher is inserted into the hollow portion 312 from the proximal end opening of the puncture needle 31, and the string 83 of the biological tissue supporting implant 81a is pushed to move in the direction toward the distal end by the pusher so that the string 83 protrudes from the distal end opening 351 of a needle tip portion 35.

With the exemplary puncture apparatus 1, similar effects to those by the second embodiment described hereinabove are achieved.

Figure 21:
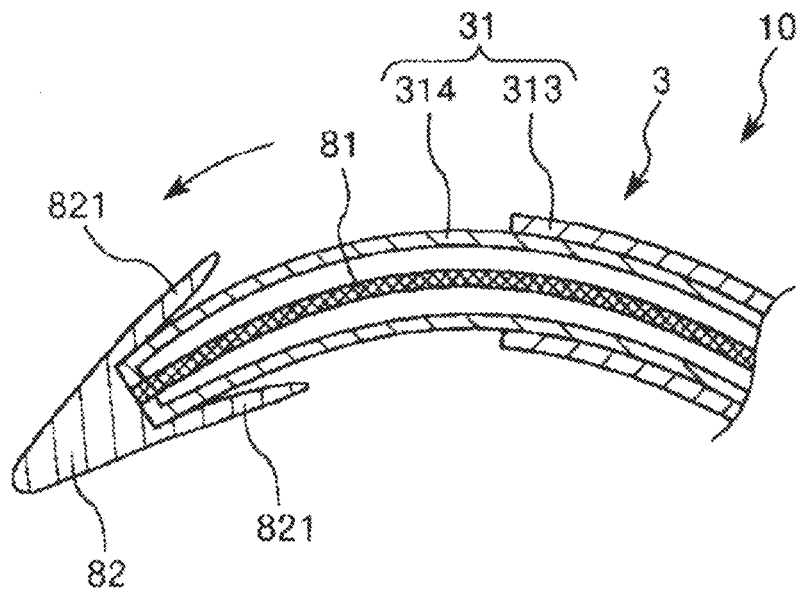
FIG. 21 is a cross sectional view depicting a puncture device according to a fourth exemplary embodiment of the puncture apparatus of the present disclosure.

FIG. 21 is a cross sectional view depicting a puncture device according to a fourth exemplary embodiment of the puncture apparatus of the present disclosure.

In the following, the fourth exemplary embodiment is described principally in regard to differences from the first exemplary embodiment described hereinabove, while the description of similar items is omitted.

In the puncture apparatus 1 of the fourth embodiment depicted in FIG. 21, the puncture needle 31 has a variable length. For example, in accordance with an exemplary embodiment, the puncture needle 31 can include a needle main body 313 for puncturing a biological tissue, and an extension needle 314 provided for relative movement to the needle main body 313 along a longitudinal direction of the needle main body 313 for puncturing a biological tissue. For example, the puncture needle 31 is extended by the extension needle 314 moving in a direction toward the distal end of the needle main body 313 with respect to the needle main body 313. Further, a hollow portion of the needle main body 313 and the extension needle 314 is open at the distal end and the proximal end of the needle main body 313 and the extension needle 314.

Further, the needle tip portion 82 of the implant assembly 8 is held removably, for example, detachably, at a distal end portion of the extension needle 314.

The puncture device 10 can include, as extension means for moving the extension needle 314 in the direction toward the distal end of the needle main body 313 with respect to the needle main body 313, a pusher not depicted which pushes the extension needle 314 to move to the direction toward the distal end of the needle main body 313.

In the exemplary puncture apparatus 1, when it is to be used, the pusher is inserted into the hollow portion of the extension needle 314 from the proximal end opening so that the extension needle 314 is pushed in the direction toward the distal end of the hollow portion of the extension needle 314 by the pusher to extend the puncture needle 31.

With the exemplary puncture apparatus 1, similar effects to those by the first exemplary embodiment described hereinabove can be achieved.

Figure 22:
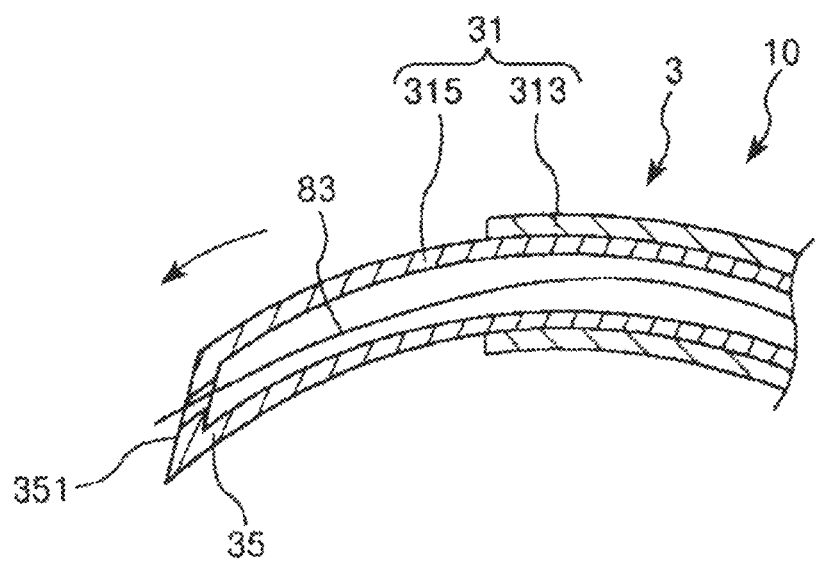
FIG. 22 is a cross sectional view depicting a puncture device according to a fifth exemplary embodiment of the puncture apparatus of the present disclosure.

FIG. 22 is a cross sectional view depicting a puncture device in a fifth exemplary embodiment of the puncture apparatus of the present disclosure.

In the following, the fifth exemplary embodiment is described principally in regard to differences from the second exemplary embodiment described hereinabove, while the description of similar items is omitted.

In the puncture apparatus 1 of the fifth embodiment depicted in FIG. 22, the puncture needle 31 can have a variable length. For example, the puncture needle 31 can include a needle main body 313 for puncturing a biological tissue, and an extension needle 315 provided for relative movement to the needle main body 313 along a longitudinal direction of the needle main body 313 for puncturing a biological tissue. For example, the puncture needle 31 is extended by movement of the extension needle 315 in a direction toward the distal end of the needle main body 313 with respect to the needle main body 313. Further, a hollow portion of the needle main body 313 and the extension needle 315 is open at both of the distal end and the proximal end.

Further, the extension needle 315 has a needle tip portion 35 at a distal end portion of the extension needle 315. In accordance with an exemplary embodiment, the needle tip portion 35 is fixed to or integrated with the distal end portion of the extension needle 315. Further, the needle tip portion 35 has a sharp needle tip at the distal end of the tip portion 35. Further, the puncture device 10 has a first pusher not depicted for pushing the string 83 of the biological tissue supporting implant 81a to move in a direction toward the distal end.

In the exemplary puncture apparatus 1, when it is used, the first pusher is inserted into the hollow portion of the extension needle 315 from the proximal end opening so that the string 83 of the biological tissue supporting implant 81a is pushed in the direction toward the distal end by the first pusher to protrude from the distal end opening 351 of the needle tip portion 35.

Further, the puncture device 10 can include, as extension means for moving the extension needle 315 in the direction toward the distal end of the needle main body 313 with respect to the needle main body 313 to extend the puncture needle 31, a second pusher for pushing the extension needle 315 to move in the direction toward the distal end of the needle main body 313.

In the exemplary puncture apparatus 1, when it is to be used, the second pusher is inserted into the hollow portion of the extension needle 315 from the proximal end opening of the same so that the extension needle 315 is pushed in the direction toward the distal end by the second pusher to extend the puncture needle 31.

With the present puncture apparatus 1, similar effects to those by the second exemplary embodiment described hereinabove are achieved.

Figure 23:
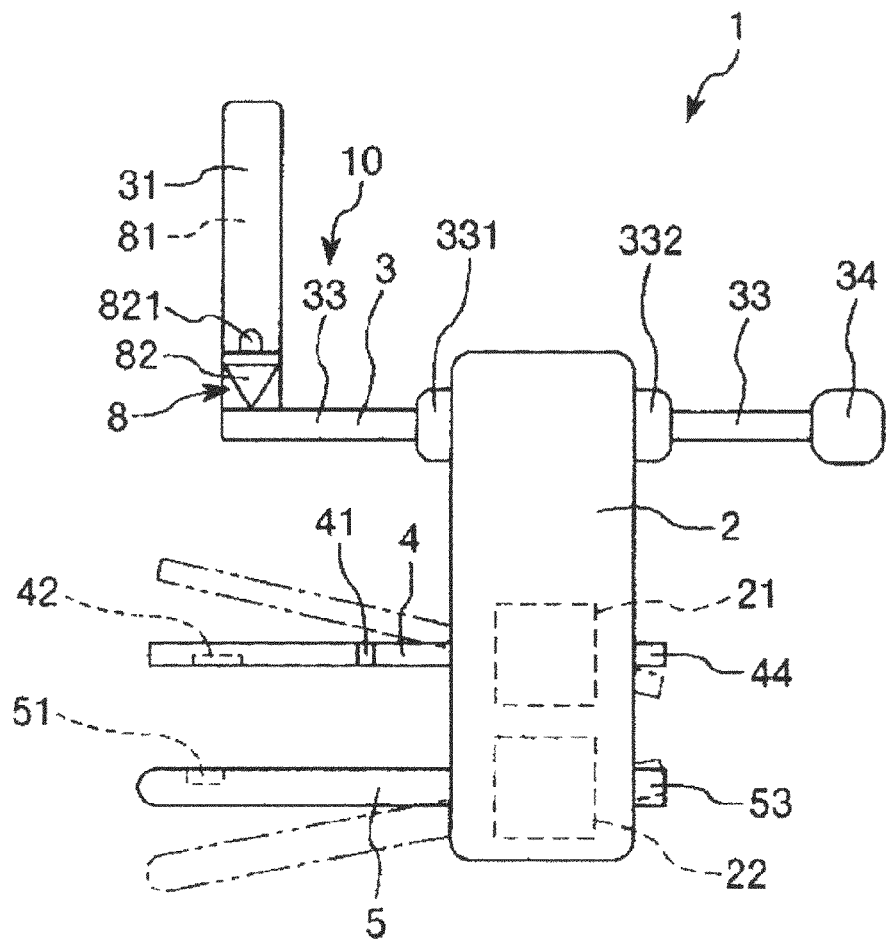
FIG. 23 is a side elevational view depicting a sixth exemplary embodiment of the puncture apparatus of the present disclosure.
Figure 24:
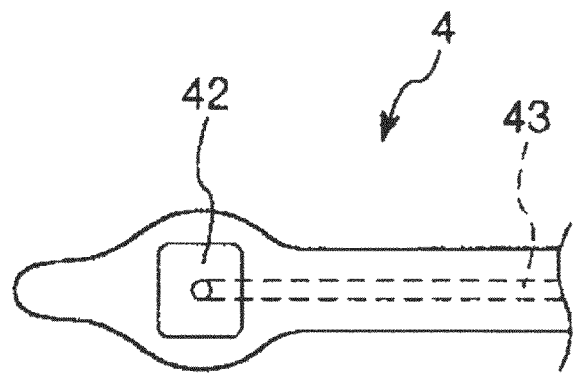
FIG. 24 is a bottom plan view depicting a urethral-insertion member of the puncture apparatus depicted in FIG. 23.
Figure 25:
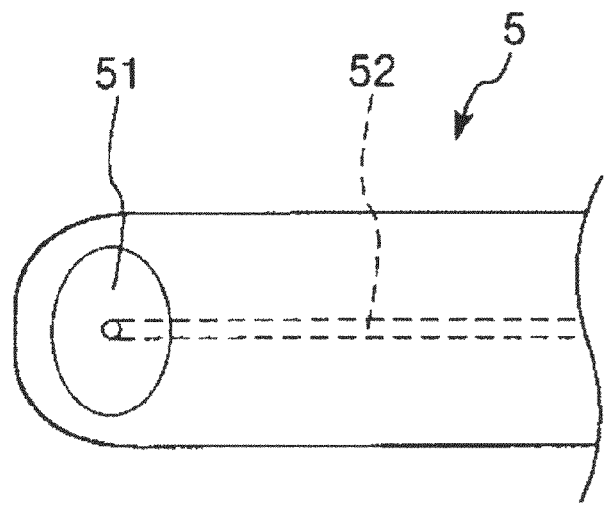
FIG. 25 is a top plan view depicting a vaginal insertion member of the puncture apparatus depicted in FIG. 23.

FIGS. 23-25 depict a sixth exemplary embodiment of the puncture apparatus of the present disclosure. In the following description, the left side in FIG. 23 is "distal end"; the right side is "proximal end"; the upper side is "upper"; and the lower side is "lower."

In the following, the sixth exemplary embodiment is described principally in regard to differences from the first exemplary embodiment described hereinabove, while the description of similar items is omitted.

As depicted in FIG. 23, the puncture apparatus 1 of the sixth exemplary embodiment is configured such that the positional relationship between the urethral-insertion member 4 and the vaginal insertion member 5 is changeable, in other words, the angle of the axial line of the urethral-insertion member 4 is changeable. For example, the supporting member 2 can include a urethral-insertion member supporting mechanism 21 capable of supporting the urethral-insertion member 4 with the angle of the axial line of the urethral-insertion member 4 changed. The urethral-insertion member supporting mechanism 21 is configured such that it can support the urethral-insertion member 4 in such a manner that a distal end portion of the urethral-insertion member 4 is directed obliquely upwardly as indicated by an alternate long and two short dashes line in FIG. 23 and can support the urethral-insertion member 4 in such a manner that the distal end portion of the urethral-insertion member 4 is directed obliquely downwardly.

Further, in the puncture apparatus 1, the angle of the axial line of the vaginal insertion member 5 can be changed. In accordance with an exemplary embodiment, the supporting member 2 can include a vaginal insertion member supporting mechanism 22 which can support the vaginal insertion member 5 with the angle of the axial line of the vaginal insertion member 5 changed. The vaginal insertion member supporting mechanism 22 is configured such that it can support the vaginal insertion member 5 in such a manner that a distal end portion of the vaginal insertion member 5 is directed obliquely downwardly as indicated by an alternate long and two short dashes line in FIG. 23 and can support the vaginal insertion member 5 in such a manner that the distal end portion of the vaginal insertion member 5 is directed obliquely upwardly.

Consequently, as indicated by the alternate long and two short dashes line in FIG. 23, the thickness of a biological tissue between the urethra and the vagina can be increased by arranging the urethral-insertion member 4 and the vaginal insertion member 5 so as to have inclined axial lines such that the distance between the axial line of the urethral-insertion member 4 and the axial line of the vaginal insertion member 5 increases toward the distal end side. Consequently, the puncture device 10 can puncture a biological tissue between the urethra and the vagina readily and with relative certainty.

Further, though not depicted, the urethral-insertion member 4 and the vaginal insertion member 5 can be arranged to have inclined axial lines such that the distance between the axial line of the urethral-insertion member 4 and the axial line of the vaginal insertion member 5 decreases toward the distal end side.

In accordance with an exemplary embodiment, the urethral-insertion member supporting mechanism 21 and the vaginal insertion member supporting mechanism 22 configure positional relationship changing means for changing the positional relationship between the urethral-insertion member 4 and the vaginal insertion member 5.

In accordance with an exemplary embodiment, the urethral-insertion member 4 has a recessed portion 42 at a lower face of a distal end portion of the urethral-insertion member 4.

The urethral-insertion member 4 can have a lumen 43 formed along an axial direction of urethral-insertion member 4. The lumen 43 is open to the proximal end of the urethral-insertion member 4 and to a bottom face of the recessed portion 42, for example, to an upper face. Further, a port 44 can be provided at the proximal end of the urethral-insertion member 4 such that it is communicated with the lumen 43. A pump not depicted can be connected to the port 44 through a pipe member not depicted. By carrying out suction by operation of the pump, a biological tissue in the urethra, for example, the inner wall of the urethra, can be attracted. Consequently, the inner wall of the urethra can be pulled with certainty by the urethral-insertion member 4, and the thickness of a biological tissue between the urethra and the vagina can be increased. Note that the recessed portion 42, lumen 43, port 44, housing and pump configure suction means.

The vaginal insertion member 5 can have a recessed portion 51 at an upper face of a distal end portion of vaginal insertion member 5.

The vaginal insertion member 5 can have a lumen 52 formed along an axial direction of the vaginal insertion member 5. The lumen 52 is open to the proximal end of the vaginal insertion member 5 and a bottom face of the recessed portion 51, for example, a lower face of the recessed portion 51. A port 53 can be provided at the proximal end of the vaginal insertion member 5 such that it is communicated with the lumen 52. A pump not depicted is connected to the port 53 through a housing not depicted such that, by carrying out suction by operation of the pump, a biological tissue in the vagina in the recessed portion 51, for example, the inner wall of the vagina, can be attracted. Consequently, the inner wall of the vagina can be pulled with relative certainty by the vaginal insertion member 5, and the thickness of the biological tissue between the urethra and the vagina can be increased. In accordance with an exemplary embodiment, the suction means can be configured from the recessed portion 51, lumen 52, port 53, housing and pump.

With the present puncture apparatus 1, effects similar to those by the first embodiment can be achieved.

Figure 26A:
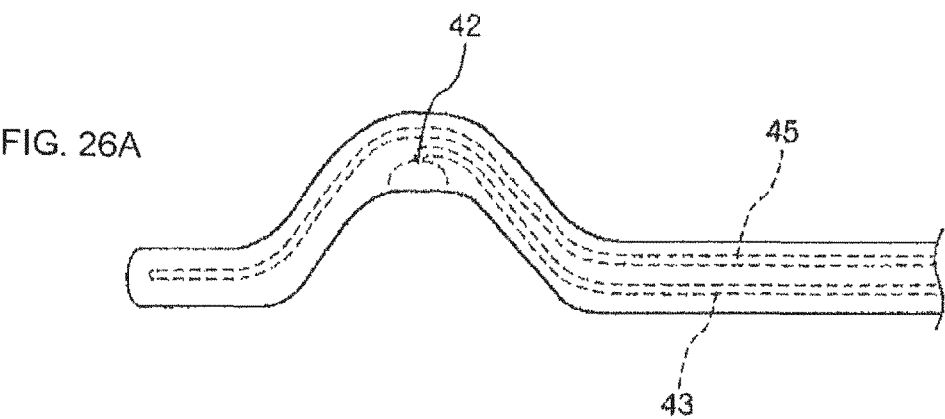
FIGS. 26(a), 26(b), and 26(c) are views depicting a urethral-insertion member and stylet in accordance with a seventh exemplary embodiment of the puncture apparatus of the present disclosure.
Figure 26B:
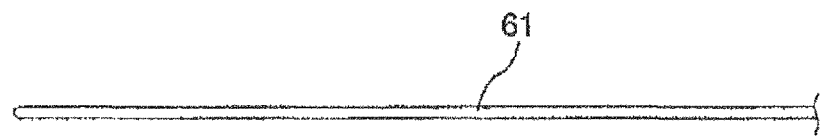
Figure 26C:
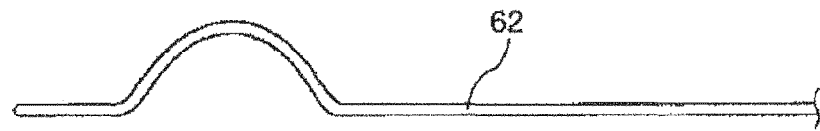

FIGS. 26(a), 26(b) and 26(c) are views depicting a urethral-insertion member and a stylet in a seventh embodiment of the puncture apparatus of the present disclosure. FIG. 26(a) is a cross sectional view depicting the urethra-insertion member, and FIGS. 26(b) and 26(c) are side elevational views depicting the stylet.

Note that, in the following, description is given assuming that the left side in FIGS. 26(a), 26(b), and 26(c) are the "distal end"; the right side is "proximal end"; the upper side is "upper"; and the lower side is "lower."

In the following, the seventh embodiment is described principally in regard to differences from the sixth embodiment described hereinabove, while the description of similar items is omitted.

As depicted in FIGS. 26(a), 26(b), and 26(c), the puncture apparatus 1 of the seventh exemplary embodiment includes a linear stylet 61 having a linear shape, and a curved stylet 62 curved at a distal end portion of puncture apparatus 1.

Further, the urethral-insertion member 4 is configured from a tube member having flexibility and exhibiting a substantially linear state in a natural state in which no external force is applied thereto. The urethral-insertion member 4 can include, in addition to the lumen 43, a lumen 45 into which the linear stylet 61 and the curved stylet 62 are selectively inserted. The lumen 45 can be formed to extend from the proximal end to a distal end portion of the urethral-insertion member 4. Further, the lumen 45 is closed at the distal end, but is open at the proximal end to the proximal end of the urethral-insertion member 4.

A port not depicted can be provided at the proximal end of the urethral-insertion member 4 such that it is communicated with the lumen 45 so that the linear stylet 61 or the curved stylet 62 can be inserted from the port.

If the linear stylet 61 is inserted into the lumen 45, then the urethral-insertion member 4 is placed into a linear state by the linear stylet 61. Consequently, the urethral-insertion member 4 can be inserted into the urethra readily and smoothly.

If the curved stylet 62 is inserted into the lumen 45, then the distal end portion of the urethral-insertion member 4 is curved by the curved stylet 62. Consequently, the thickness of a biological tissue between the urethra and the vagina can be increased. Consequently, the puncture device 10 can puncture a biological tissue between the urethra and the vagina readily and with relative certainty.

With the present puncture apparatus 1, similar to effects to those by the sixth exemplary embodiment described hereinabove can be achieved.

Although the puncture device and the puncture apparatus of the present disclosure have been described on the basis of the embodiments depicted in the drawings, the present disclosure is not limited to them, and the configuration of each unit can be replaced with an arbitrary configuration having a similar function. Further, other arbitrary constructions may be added to the present disclosure.

In accordance with an exemplary embodiment, the present disclosure may be a combination of two or more configurations of the exemplary embodiments disclosed herein.

Further, in the present disclosure, for example, the vaginal insertion member may be omitted while the restriction means is configured such that it restricts only the positional relationship between the puncture needle (puncture member) and the vaginal insertion member.

In the description of the embodiments described above, the puncture device and the puncture apparatus of the present disclosure are applied to an apparatus which is used when a biological tissue supporting implant which can be buried for the treatment of the woman's urinary incontinence is buried into the living body. However, the application of the puncture device and the puncture apparatus of the present disclosure are not limited to this.

For example, the target of the application of the present disclosure includes an excretory disorder along with the weakening of the pelvic floor muscle group (urinary urgency, frequent urination, urinary incontinence, fecal incontinence, urinary retention, dysuria or the like), and a pelvic floor disorder including pelvic organ prolapse, vesicovaginal fistula, urethrovaginal fistula, pelvic pain or the like. In the pelvic organ prolapse, there are include disorders of cystocele, enterocele, rectocele, hysterocele and the like. Alternatively, there are included disorders of anterior vaginal prolapse, posterior vaginal prolapse, vaginal vault prolapse, vaginal apical prolapse and the like in which the naming method thereof is based on the manipulating vaginal-wall regions.

Also, in the overactive tissues, there are included bladder, vagina, uterus, bowel and the like. In the less active tissues, there are included bones, muscles, fascias, ligaments and the like. For example, in the pelvic floor disorders, there are included an obturator fascia, a coccygeus fascia, a cardinal ligament, an uterosacral ligament, a sacrotuberous ligament and the like.

For the procedure for interlocking an overactive tissue in the pelvic floor disorder with the less active tissue, there are included a retropubic sling surgery, a transobturator sling surgery (transobturator sling surgery, transobturator tape: TOT), a tension-free vaginal mesh (Tension-free Vaginal Mesh: TVM) surgery, a uterosacral ligament suspension (Uterosacral Ligament Suspension: USLS) surgery, a sacrospinous ligament fixation (Sacrospinous Ligament Fixation: SSLF) surgery, an iliococcygeus fascia fixation surgery, a coccygeus fascia fixation surgery, and the like.

The puncture device of the present disclosure can include a puncture needle having a hollow portion, a needle tip portion positioned at a distal end of the puncture needle and configured to puncture a biological tissue, and an elongated biological tissue supporting implant accommodated in the hollow portion of the puncture needle and configured to be buried into a living body to support the biological tissue.

Meanwhile, the puncture apparatus of the present disclosure can include the puncture device according to the present disclosure, a urethral-insertion member of a longitudinal shape configured to be inserted into a urethra, and restriction means for restricting, when the puncture device is rotationally moved to puncture a biological tissue, a positional relationship between the puncture device and the urethral-insertion member such that the needle tip portion passes at a farther-position side from the center of rotational movement of the puncture device than the urethral-insertion member.

In accordance with an exemplary embodiment, a biological tissue supporting implant can be buried into a living body readily, and when the biological tissue supporting implant is buried, the burden on the patient is light and the safety of the patient is high. In addition, the safety of the operator is relatively high.

In accordance with an exemplary embodiment, where the puncture apparatus includes the restriction means for restricting the positional relation between the puncture device and the urethral-insertion member such that, when the puncture device rotationally moves to puncture the biological tissue, the needle tip portion passes the farther-position side from the center of rotational movement of the puncture device than the urethral-insertion member, for example, when the puncture apparatus is to be used for the treatment of woman's urinary incontinence, the urethral-insertion member of the puncture apparatus is inserted into a urethra, and the puncture device is rotationally moved so that the living body is punctured by the puncture device. Thereupon, since the needle tip portion passes the farther-position side from the center of the puncture device than the urethral-insertion member, the puncture device can puncture the living body avoiding the urethra. Consequently, the puncture device can be prevented from puncturing the urethra. Further, the puncture device can help prevent the fingertip of the operator from being punctured by the puncture device.

Further, when the biological tissue supporting implant for the treatment of urinary incontinence is to be buried, no incision of the vaginal wall is necessary, and the biological tissue supporting implant can be buried by a low invasive manual procedure. Further, such a situation that, as in a case in which the vagina is incised, the biological tissue supporting implant is exposed to the inside of the vagina through a wound caused by the incision or that such complications as an infection from the wound occur can be prevented. Therefore, the biological tissue supporting implant can be buried in relatively high safety and with relative certainty.

Further, since the biological tissue supporting implant is accommodated in the hollow portion of the puncture needle, the biological tissue supporting implant can be buried into a living body readily.

The detailed description above describes a puncture instrument and puncture device. The disclosure is not limited, however, to the precise embodiments and variations described. Various changes, modifications and equivalents can effected by one skilled in the art without departing from the spirit and scope of the disclosure as defined in the accompanying claims. It is expressly intended that all such changes, modifications and equivalents which fall within the scope of the claims are embraced by the claims.

What is claimed is:

1. A puncture apparatus, comprising:
   a puncture device configured to have a rotational motion, the puncture device having a shaft portion configured to provide a rotational axis of the rotational motion, the puncture device comprising:
      a puncture needle having a hollow portion, the puncture needle having a portion curved along a longitudinal direction of the puncture needle;
      a needle tip portion positioned at a distal end of the puncture needle and configured to puncture a biological tissue; and
      an elongated biological tissue supporting implant accommodated in the hollow portion of the puncture needle and configured to be buried into a living body to support the biological tissue;
   a urethral-insertion member of a longitudinal shape configured to be inserted into a urethra; and
   restriction means for restricting, when the puncture device is rotationally moved to puncture the biological tissue, a positional relationship between the puncture device and the urethral-insertion member such that the needle tip portion passes from a center of rotational movement of the puncture device beyond the urethral-insertion member between the urethra and a vagina in a plane perpendicular to an axial line of the shaft portion, and wherein the shaft portion is arranged in a spaced relationship by a predetermined distance from the urethral-insertion member such that the axial line of the shaft portion and an axial line of the urethral-insertion member extend in parallel to each other.

2. The puncture apparatus according to claim 1, further comprising:
   a vaginal insertion member of a longitudinal shape configured to be inserted into the vagina, wherein the restriction means restricts a positional relationship between the puncture device and the vaginal insertion member such that, when the puncture device is rotationally moved to puncture a biological tissue, the needle tip portion does not collide with the vaginal insertion member.

3. The puncture apparatus according to claim 2, wherein the restriction means includes a supporting member which supports the shaft portion for rotational movement and supports the urethral-insertion member and the vaginal insertion member.

4. The puncture apparatus according to claim 3, wherein at least one of the urethral-insertion member and the vaginal insertion member has provided thereon suction means capable of attracting a biological tissue thereto.

5. The puncture apparatus according to claim 3, wherein the positional relationship between the urethral-insertion member and the vaginal insertion member is variable.

6. The puncture apparatus according to claim 2, wherein at least one of the urethral-insertion member and the vaginal insertion member has provided thereon suction means capable of attracting a biological tissue thereto.

7. The puncture apparatus according to claim 6, wherein the positional relationship between the urethral-insertion member and the vaginal insertion member is variable.

8. The puncture apparatus according to claim 2, wherein the positional relationship between the urethral-insertion member and the vaginal insertion member is variable.

9. A method of forming a path in a living body comprising:
- placing a puncture needle of a puncture device into a portion of the living body, the puncture needle having a hollow portion, a curved portion along a longitudinal direction of the puncture needle, and a needle tip portion positioned at a distal end of the puncture needle and configured to puncture a biological tissue, the puncture device having a shaft portion having a shaft portion configured to provide a rotational axis;
- accommodating an elongated biological tissue supporting implant in the hollow portion of the puncture needle and configured to be buried into the living body to support the biological tissue;
- inserting an urethral-insertion member of a longitudinal shape into a urethra; and
- restricting, when the puncture device is rotationally moved to puncture the biological tissue, a positional relationship between the puncture device and the urethral-insertion member such that the needle tip portion passes from a center of rotational movement of the puncture device beyond the urethral-insertion member between the urethra and a vagina in a plane perpendicular to an axial line of the shaft portion, and wherein the shaft portion is arranged in a spaced relationship by a predetermined distance from the urethral-insertion member such that the axial line of the shaft portion and an axial line of the urethral-insertion member extend in parallel to each other.

10. The method according to claim 9, comprising:
- burying the elongated biological tissue supporting implant into the living body to support the biological tissue.

\* \* \* \* \*